US012758684B2

(12) United States Patent
Radenkovic et al.

(10) Patent No.: US 12,758,684 B2
(45) Date of Patent: Oct. 13, 2026

(54) IMPLANT FOR OVARIAN DECLINE AND METHODS OF MANUFACTURING AN IMPLANT FOR OVARIAN DECLINE

(71) Applicant: Gameto, Inc, New York, NY (US)

(72) Inventors: Dina Radenkovic, New York, NY (US); Christian Kramme, New York, NY (US); Martin Varsavsky, New York, NY (US)

(73) Assignee: Gameto, Inc., Austin, TX (US)

( * ) Notice: Subject to any disclaimer, the term of this patent is extended or adjusted under 35 U.S.C. 154(b) by 402 days.

(21) Appl. No.: 18/224,687

(22) Filed: Jul. 21, 2023

(65) Prior Publication Data

US 2024/0050625 A1 Feb. 15, 2024

Related U.S. Application Data

(63) Continuation of application No. 17/886,773, filed on Aug. 12, 2022, now Pat. No. 11,744,920.

(51) Int. Cl.

| | |
|---|---|
| ***A61L 27/38*** | (2006.01) |
| ***A61K 9/00*** | (2006.01) |
| ***A61K 35/12*** | (2015.01) |
| ***A61L 27/24*** | (2006.01) |
| ***A61L 27/36*** | (2006.01) |
| ***C12N 5/00*** | (2006.01) |

(52) U.S. Cl.

CPC ............ *A61L 27/38* (2013.01); *A61K 9/0024* (2013.01); *A61K 35/12* (2013.01); *A61L 27/24* (2013.01); *A61L 27/3633* (2013.01); *C12N 5/0012* (2013.01); *C12N 5/0068* (2013.01); *C12N 2533/90* (2013.01)

(58) Field of Classification Search

CPC ........................................................ A61L 27/38

See application file for complete search history.

(56) References Cited

U.S. PATENT DOCUMENTS 10,392,601 B2 8/2019 Romero et al.
10,792,311 B2 10/2020 Cheng et al.

(Continued)

FOREIGN PATENT DOCUMENTS

WO WO-2009/138855 A2 11/2009
WO WO-2010003020 A1 1/2010

(Continued)

OTHER PUBLICATIONS

Chen et al, Autologous Implantation of Thecal Cells Restores Ovarian Function in Non-Human Primates, Cell Discovery, 7:75. (Year: 2021).*

(Continued)

*Primary Examiner* — Carlos A Azpuru

(74) *Attorney, Agent, or Firm* — Clark & Elbing LLP

(57) ABSTRACT

An implant for ovarian decline is provided. The implant includes at least an engineered ovarian support cell, an extracellular matrix substrate, and a delivery apparatus. In some embodiments, the at least an engineered ovarian support cell includes an engineered granulosa cell. In other embodiments, the at least an engineered ovarian support cell includes an engineered lutein cell. In other embodiments, the at least an engineered ovarian support cell includes an engineered theca cell.

3 Claims, 7 Drawing Sheets

(56) References Cited

U.S. PATENT DOCUMENTS

| | | | |
|---|---|---|---|
| 11,744,920 B1 * | 9/2023 | Radenkovic ........ | A61L 27/3633 424/423 |
| 11,802,268 B1 | 10/2023 | Kramme et al. | |
| 2006/0194235 A1 | 8/2006 | Chen et al. | |
| 2013/0089870 A1 | 4/2013 | Yamanaka et al. | |
| 2015/0359822 A1 | 12/2015 | Atwood | |
| 2016/0001051 A1 | 1/2016 | Kumar et al. | |
| 2016/0010151 A1 * | 1/2016 | Fan ..................... | C12Q 1/6874 506/14 |
| 2016/0237402 A1 | 8/2016 | Tilly et al. | |
| 2017/0290890 A1 | 10/2017 | Cheng et al. | |
| 2018/0015127 A1 | 1/2018 | Ichim et al. | |
| 2018/0251729 A1 | 9/2018 | Obata et al. | |
| 2019/0288915 A1 | 9/2019 | Denyer et al. | |
| 2020/0279635 A1 | 9/2020 | Letterie et al. | |
| 2021/0261922 A1 | 8/2021 | Nagamatsu et al. | |
| 2021/0290632 A1 | 9/2021 | Freedman et al. | |
| 2022/0010270 A1 | 1/2022 | Sivanandane et al. | |
| 2022/0399091 A1 | 12/2022 | Loewke et al. | |

FOREIGN PATENT DOCUMENTS

| | | |
|---|---|---|
| WO | WO-2012/121874 A1 | 9/2012 |
| WO | WO-2016094970 A1 | 6/2016 |
| WO | WO-2017047799 A1 | 3/2017 |
| WO | WO-2020/072977 A1 | 4/2020 |
| WO | WO-2020/225085 A1 | 11/2020 |
| WO | WO-2023/192934 A2 | 10/2023 |
| WO | WO-2023/250101 A1 | 12/2023 |
| WO | WO-2024/206245 A1 | 10/2024 |

OTHER PUBLICATIONS

Sittadjody et al., "Encapsulation of Mesenchymal Stem Cells in 3D Ovarian Cell Constructs Promotes Stable and Long-Term Hormone Secretion with Improved Physiological Outcomes in a Syngeneic Rat Model," Ann Biomed Eng. 48(3):1058-1070 (Mar. 2020).

Hillier et al., "Role of androgens in follicle maturation and atresia," Baillieres Clin Obstet Gynaecol. 11(2):249-60 (Jun. 1997).

Singh et al., "Gonadotropins as pharmacological agents in assisted reproductive technology and polycystic ovary syndrome," Trends Endocrinol Metab. 34(4):194-215 (Apr. 2023).

Johnson et al., "Effect of human granulosa cell co-culture using standard culture media on the maturation and fertilization potential of immature human oocytes," Fertil Steril. 90(5):1674-9 (Nov. 2008).

Torre et al., "In vitro maturation of human oocytes in a follicle-mimicking three-dimensional coculture," Fertil Steril. 86(3):572-6 (Sep. 2006).

Trounson et al., "In vitro maturation and the fertilization and developmental competence of oocytes recovered from untreated polycystic ovarian patients," Fertil Steril. 62(2):353-62 (Aug. 1994).

Dandekar et al., "Maturation of immature oocytes by coculture with granulosa cells," Fertil Steril. 55(1):95-9 (Jan. 1991).

Schramm et al., "Granulosa cells from follicle stimulating hormone-primed monkeys enhance the developmental competence of in-vitro-matured oocytes from non-stimulated rhesus monkeys," Hum Rprod. 11(8):1698-702 (Aug. 1996).

Zhang et al., "A flexible short protocol in women with poor ovarian response over 40 years old," J Ovarian Res. 14(1):1-8 (Jan. 2021).

Devroey et al., "Clinical outcome of a pilot efficacy study on recombinant human follicle-stimulating hormone (Org 32489) combined with various gonadotrophin-releasing hormone agonist regimens," Hum Reprod. 9(6):1064-1069 (Jun. 1994).

Prasannan et al., "IoT based Device for Fertility Monitoring," 2020 5th International Conference on Communication and Electronics Systems (ICCES), Jun. 10-12, Coimbatore, India. (2020) (5 pages).

Lazzaroni-Tealdi et al. "Oocyte Scoring Enhances Embryo-Scoring in Predicting Pregnancy Chances with IVF Where It Counts Most." PLoS One. 10(12):e0143632 (Dec. 2015) (13 pages).

Virant-Klun et al., "Human oocyte maturation in vitro is improved by co-culture with cumulus cells from mature oocytes," Reprod Biomed Online. 36(5):508-523 (May 2018).

Pongsuthirak et al., "Comparison of Blastocyst and Sage Media for In Vitro Maturation of Human Immature Oocytes," Reprod Sci. 22(3):343-346 (Mar. 2015).

Lonergan et al., "Maturation of Oocytes in Vitro," Annu Rev Anim Biosci. 4:255-268 (2016) (16 pages).

Velletri et al., "Single cell-derived spheroids capture the self-renewing subpopulations of metastatic ovarian cancer," Cell Death Differ. 29(3):614-626 (Mar. 2022).

Yoon et al., "Integration of Genomic Profiling an Organoid Development in Precision Oncology," Int J Mol Sci. 23(1):216 (Dec. 2021) (15 pages).

Kopper et al., "An organoid platform for ovarian cancer captures intra- and interpatient heterogeneity," Nat Med. 25(5):838-849 (May 2019) (27 pages).

Lukonin et al., "Organoids in image-based phenotypic chemical screens," Exp Mol Med. 53(10):1495-1502 (Oct. 2021).

Smela et al., "Directed differentiation of human iPSCs to functional ovarian granulosa-like cells via transcription factor overexpression," Elife. 12:e83291 (Feb. 2023) (29 pages).

Ng et al., "A comprehensive library of human transcription factors for cell fate engineering," Nat Biotechnol. 39(4):510-519 (Apr. 2021) (18 pages).

Kramme et al., "An integrated pipeline for mammalian genetic screening," Cell Rep Methods. 1(6):100082 (Sep. 2021) (20 pages).

Pongsuthirak et al., "Comparison of Medicult and Sage Media for In Vitro Maturation of Immature Oocytes Obtained during Cesarean Deliveries," JFIV Reprod Med Genet. 3(1): 1-4 (Dec. 2014) (5 pages).

Kobayashi et al., "Principles of early human development and germ cell program from conserved model systems," Nature. 546(7658):416-420 (Jun. 2017).

Heidari-Khoei et al., "Organoid technology in female reproductive biomedicine," Reprod Biol Endocrinol. 18(1):64 (Jun. 2020) (19 pages).

Stejskalová et al., "In vitro modelling of the physiological and diseased female reproductive system," Acta Biomater. 132:288-312 (Sep. 2021).

Lipskind et al., "An Embryonic and Induced Pluripotent Stem Cell Model for Ovarian Granulosa Cell Development and Steroidogenesis," Reproductive Sciences. 25(5):712-726 (Aug. 2017).

Lan et al., "Differentiation of Human Embryonic Stem Cells Into Functional Ovarian Granulosa-like Cells," J Clin Endocrinol Metab. 98(9):3713-23 (Sep. 2013).

Smela et al., "Directed Differentiation of Human iPSCs to Functional Ovarian Granulosa-Like Cells via Transcription Factor Overexpression," bioRxviv. doi: https://doi.org/10.1101/2022.07.04.498717 (Jul. 2022) (21 pages).

Combelles et al., "In vitro maturation of human oocytes and cumulus cells using a co-culture three-dimensional collagen gel system," Hum Reprod. 20(5):1349-58 (May 2005).

Hofmann et al., "High-Dose Follicle-Stimulating Hormone (FSH) Ovarian Stimulation in Low-Responder Patients for in Vitro Fertilization," J In Vitro Fert Embryo Transf. 6(5):285-9 (Oct. 1989).

Fatemi et al., "Dose adjustment of follicle-stimulating hormone (FSH) during ovarian stimulation as part of medically-assisted reproduction in clinical studies: a systematic review covering 10 years (2007-2017)," Reprod Biol Endocrinol. 19(1):68 (May 2021) (15 pages).

N A Ho et al., "The effectiveness and safety of in vitro maturation of oocytes versus in vitro fertilization in women with a high antral follicle count," Hum Reprod. 34(6):1055-1064 (Jun. 2019).

Fadini et al., "Effect of different gonadotrophin priming on IVM of oocytes from women with normal ovaries: a prospective randomized study," Reprod Biomed Online. 19(3):343-351 (Sep. 2009) (10 pages).

Fadini et al., "Oocyte in vitro maturation in normo-ovulatory women." Fertility and sterility 99(5) (Apr. 2013): 1162-1169.

Vuong et al., "Live births after oocyte in vitro maturation with a prematuration step in women with polycystic ovary syndrome," J Assist Reprod Genet. 37(2):347-357 (Feb. 2020).

(56) References Cited

OTHER PUBLICATIONS

Paulsen et al., "Translation of a human induced pluripotent stem cell-derived ovarian support cell product to a Phase 3 enabling clinical grade product for in vitro fertilization treatment," medRxiv. (Apr. 5, 2025) (44 pages).
Cakmak et al., "Metaphase II (MII) oocytes obtained at different time points in the same in vitro fertilization cycle," J Assist Reprod Genet. 29:1203-1205 (Sep. 2012).
De Roo et al., "In Vitro Maturation of Oocytes Retrieved from Ovarian Tissue: Outcomes from Current Approaches and Future Perspectives," J Clin Med. 10:4680 (Oct. 2021) (15 Pages).
Turathum et al., "The Function of Cumulus Cells in Oocyte Growth and Maturation and in Subsequent Ovulation and Fertilization," Cells. 10(9):2292 (Sep. 2021) (18 Pages).
Motlik et al., "Co-culture with pig membrana granulose cells modulates the activity of CDK1 and MAP kinase in maturing cattle oocytes," Zygote. 4(3): 247-256. (Sep. 1996).
Abdel-Ghani et al., "In vitro maturation of canine oocytes co-cultured with bovine and canine granulosa cell monolayers," Theriogenology. 77(2):347-355 (Jan. 2012) (10 pages).
Yamashiro et al., "Generation of human oogonia from induced pluripotent stem cells in vitro," Science. 362(6512):356-360 (Oct. 2018) (47 pages).
Yoshino et al., "Generation of ovarian follicles from mouse pluripotent stem cells," Science. 373(6552):eabe0237 (Jul. 2021).
Corfman et al., "A novel ovarian stimulation protocol for use with the assisted reproductive technologies," Fertil Steril. 60(5):864-70 (Nov. 1993).
Sittadjody et al., "In vivo transplantation of 3D encapsulated ovarian constructs in rats corrects abnormalities of ovarian failure," Nat Commun. 8(1):1858 (Dec. 2017) (13 pages).
Chen et al., "Autologous transplantation of thecal stem cells restores ovarian function in nonhuman primates," Cell Discov. 7(1):75 (Aug. 2021) (16 pages).
Park et al., "Ovarian-Cell-Like Cells from Skin Stem Cells Restored Estradiol Production and Estrus Cycling in Ovariectomized Mice," Stem Cells Dev. 23(14):1647-1658 (Jul. 2014).
Yoon et al., "Hormone autocrination by vascularized hydrogel delivery of ovary spheroids to rescue ovarian dysfunctions," Sci Adv. 7(18):eabe8873 (Apr. 2021) (15 pages).
De Vos et al., "Clinical outcome of non-hCG-primed oocyte in vitro maturation treatment in patients with polycystic ovaries and polycystic ovary syndrome," Fertil Steril. 96(4):860-864 (Oct. 2011) (5 pages).
Bothun et al., "Steps toward the generation of ovarian somatic cells from pluripotent stem cells," Clinical Theriogenology. 12(4):529-535 (Dec. 2020).
Frobel et al., "Epigenetic Rejuvenation of Mesenchymal Stromal Cells Derived from Induced Pluripotent Stem Cells," Stem Cell Reports. vol. 3:414-422 (2014) (9 pages).
Horvath, "DNA methylation age of human tissues and cell types," Genome Biology. 14:R115 (2013) (19 pages).
Itami et al., "Age-associated changes in bovine oocytes and granulosa cell complexes collected from early antral follicles," J Assist Reprod Genet. 31:1079-1088 (2014) (10 pages).
Jahromi et al., "The potential role of granulosa cells in the maturation rate of immature human oocytes and embryo development: A co-culture study," Clin Exp Reprod Med. 42(3):111-7 (Sep. 2015).
Liu et al., "Transplantation of ovarian granulosa-like cells derived from human induced pluripotent stem cells for the treatment of murine premature ovarian failure," Molecular Medicine Reports. 13:5053-5058 (2016) (10 pages).
Paulsen et al., "Development of human induced pluripotent stem cell-derived ovarian support cells as a clinical-grade product for in vitro fertilization," Cell Stem Cell. 33:1-15 (includes supplemental content) (Jan. 2026) (45 pages).
Piechota et al., "Human-induced pluripotent stem cell-derived ovarian support cell co-culture improves oocyte maturation in vitro after abbreviated gonadotropin stimulation," Hum Reprod. 38(12):2456-2469 (Dec. 2023).

* cited by examiner

IMPLANT FOR OVARIAN DECLINE AND METHODS OF MANUFACTURING AN IMPLANT FOR OVARIAN DECLINE

CROSS-REFERENCE TO RELATED APPLICATIONS

This application is a continuation of Non-provisional application Ser. No. 17/886,773 filed on Aug. 12, 2022, and entitled "IMPLANT FOR OVARIAN DECLINE AND METHODS OF MANUFACTURING AN IMPLANT FOR OVARIAN DECLINE," the entirety of which is incorporated herein by reference.

FIELD OF THE INVENTION

The present invention generally relates to the field of hormone replacement therapy. In particular, the present invention is directed to an implant for ovarian decline.

BACKGROUND

Current hormone replacement methods are insufficient in combating ovarian decline. One of the reasons being that hormone replacement therapy replace hormones at fixed dose each day. There is a need for hormone replacement techniques that allow for personalized physiological based delivery of hormones.

SUMMARY OF THE DISCLOSURE

In another aspect, a method for reversing ovarian decline includes obtaining a baseline hormone level relating to a user; and manufacturing an implant for ovarian decline as a function of the baseline hormone level.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for reversing ovarian decline.

Aspects of the present disclosure can be used to reverse ovarian decline in a person by providing personalized cyclic dosing of hormones into a user. Aspects of the present disclosure can also be used as an ectopic ovarian hub to secrete replacement hormones into a user.

Figure 1:
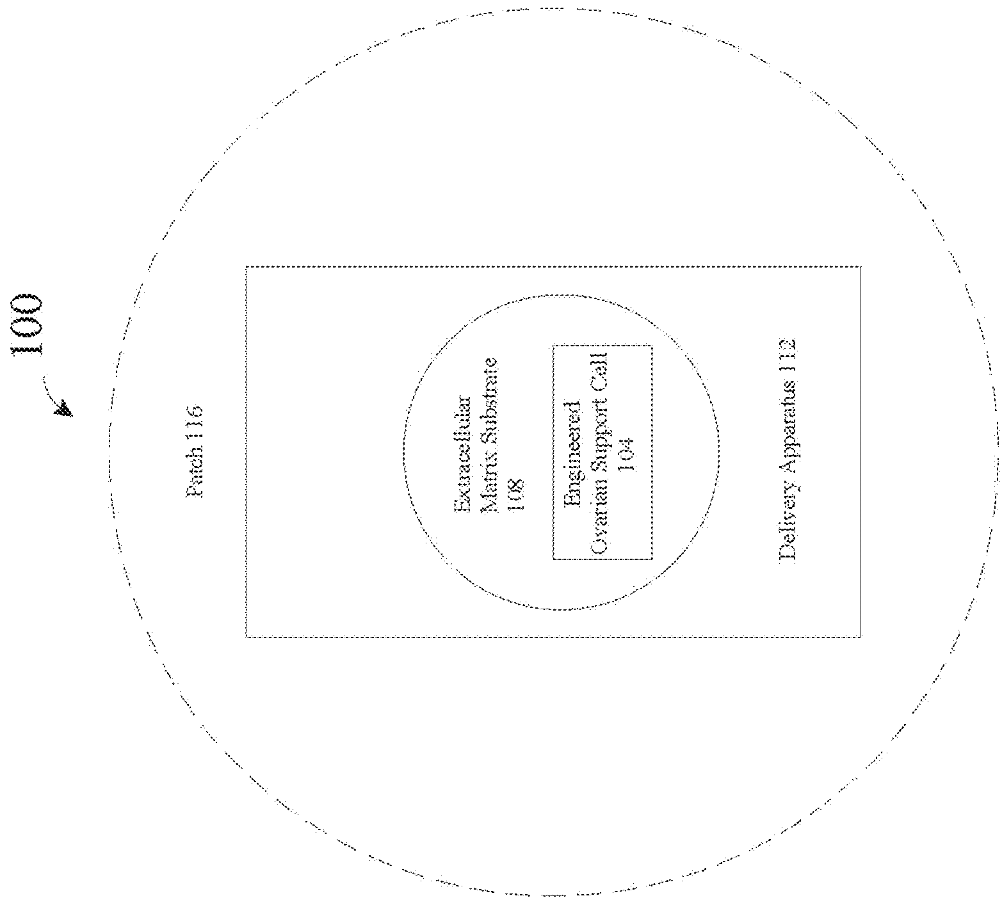
FIG. 1 is an exemplary embodiment of an implant for ovarian decline.

Referring now to the drawings, FIG. 1 illustrates an exemplary method of an implant 100 for ovarian decline. The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

Still referring to FIG. 1, an "implant," as used in this disclosure, is a device applied to and/or inserted into a living being. A "living being," as used in this disclosure, is any organism or life form that is alive. A living being may include a human being, an animal, a plant, a fungus, and the like. An implant may replace a missing biological structure, support a damaged biological structure, and/or enhance an existing biological structure of a living being. An implant may deliver a therapeutically effective amount of a substance directly to a target tissue and/or the bloodstream. A "substance," as used in this disclosure, is a matter of particular or definite chemical constitution. A substance may be a drug product, or biological substance such as engineered ovarian support cell (described further below). For example, a drug product may include hormones such estrogen, progesterone, and/or testosterone. A dug product may include a class of antidepressants, anticonvulsants, anesthetics, anti-addiction agents, antibacterial, antidementia agents, and/or antifungals. For example, a substance may include selective serotonin reuptake inhibitors (SSRIs), and/or gabapentin. A drug product may include an herbal remedy like black cohosh, *Agnus castus*, shatavari, *Withania somnifera*, and Maca. Implant 100 may be a medical device made of a biomedical material such as titanium, silicone, apatite, and the like. Implant 100 may deliver medication, monitor body functions, or provide support to organs and tissues. In an embodiment, implant 100 may be placed permanently in a living being. In an embodiment, implant 100 may be removeable. "Permanently," as used in this disclosure is the placement of an implant as a bio-structure substitute. For example, permanent dentures are false teeth that are affixed to the bone in the jaw. These implant dentures are not removable like common dentures. Implant 100 may act as a permanent ectopic ovarian hub to replace the function of a user's ovary in hormone production. "Removable," as used in this disclosure, is the temporary placement of implant to carry out a specific function. For example, contraceptive implants may be placed in a user only for a certain period, such as 5 years, before being removed. Implant 100 may be removed from a user after reversing symptoms or levels of ovarian decline. For example, implant 100 may be removed after an hour, day, week, and/or month.

Still referring to FIG. 1, in an embodiment, implant 100 may be a contraceptive implant. A "contraceptive implant," as used in this disclosure, is an implantable medical device used for the purpose of birth control "Birth control," as used in this disclosure, is any method, medicine, or device used to prevent pregnancy. Other uses of a contraceptive implant may include, regulating menstrual cycles, preventing ovarian cysts, relieving premenstrual syndrome symptoms, relieving polycystic ovarian syndrome (PCOS) symptoms, relieving dysmenorrhea symptoms, and lowering migraines. Implant 100 may depend on the timed release of hormones to hinder ovulation or sperm development, the ability of copper to act as a natural spermicide within the uterus, or it may work using a non-hormonal, physical blocking mechanism. For example, implant 100 may be an intrauterine device (IUD), which as used in this disclosure, is a small contraceptive device, often 'T'-shaped, which is implanted into the uterus. IUD can be hormonal or non-hormonal are long-acting, reversible. In an embodiment, implant 100 may be porous implant. A porous implant, as used in this disclosure, is an implant made of porous material such as titanium. Porous implants are characterized by the presence of voids in the metallic or ceramic matrix. Voids can be regular, such as in additively manufactured (AM) lattices, or stochastic, such as in gas-infiltrated production processes.

Still referring to FIG. 1, implant 100 is utilized for ovarian decline. "Ovarian decline," as used in this disclosure, is a decline in ovarian function. A decline in ovarian function may cause a female to lose her normal reproductive potential. A loss of normal reproductive potential may manifest as one or more conditions including but not limited to infertility, primary ovarian insufficiency (POI), poly cystic ovarian syndrome (PCOS), menopause, endometriosis, uterine fibroids, gynecological cancer, interstitial cystitis, pelvic inflammatory disease (PID), vaginitis, cervical dysplasia, uterine fibroids, pelvic floor prolapse, interstitial cystitis, and the like. Ovarian decline may manifest in a variety of uncomfortable or even life threating conditions. In medicine, "comorbidity" is the presence of one or more additional conditions often co-occurring with a primary condition. Comorbidity describes the effect of all other conditions an individual patient might have other than the primary condition of interest and can be physical or psychological. Comorbidities of ovarian decline may include but is not limited to dementia, depression, strokes, cardiovascular disease, arthritis, osteoporosis, anxiety, menopause, hypothyroidism, low libido, and similar conditions. "Dementia," as used in this disclosure, is a chronic or persistent disorder of the mental processes caused by brain disease or injury and marked by memory disorders, personality changes, and impaired reasoning. If the body does not produce sufficient levels of hormones (i.e., thyroid hormone), the neurotransmitters cannot function properly. Memory span and ability to concentrate will be negatively affected. As the body's estrogen levels decrease, which happens before and during menopause, estrogen can no longer participate in brain function as it normally had. This can cause occasional lapses in brain function, resulting in short-term memory issues. "Depression," as used in this disclosure, is a mood disorder that causes a persistent feeling of sadness and loss of interest. The reduction, continued deficit, and or changes in levels of estrogens throughout the menstrual cycle are correlated with mood-related distress. A "stroke," as used in this disclosure, is a biological occurrence where something blocks blood supply to part of the brain or when a blood vessel in the brain bursts. A long period of estrogen deprivation can lead to loss of sensitivity and protective effects in the brain and weaken areas normally resistant to stroke damage.

Still referring to FIG. 1, in an embodiment, implant 100 may contain electronic artificial pacemakers, cochlear implants, and the like. Implant 100 may be bioactive, such as a subcutaneous drug delivery device in the form of implantable pills or drug-eluting stents. Implant 100 may be used in a sensory/neurological based application for disorders affecting the major senses and the brain, as well as other neurological disorders. For example, implant 100 may be used in the treatment of conditions such as cataract, glaucoma, keratoconus, and other visual impairments; otosclerosis and other hearing loss issues, as well as middle ear diseases such as otitis media; and neurological diseases such as epilepsy, Parkinson's disease, and treatment-resistant depression.

Still referring to FIG. 1, in an embodiment, implant 100 may be a transdermal patch. A transdermal patch, as used in this disclosure, is a medicated adhesive patch that is placed on the skin to deliver a specific dose of any substance, as described above, through the skin and into the bloodstream. For example, implant 100 may be a single-layer drug-in-Adhesive, the adhesive layer of this system also contains the drug. In this type of patch, the adhesive layer not only serves to adhere the various layers together, along with the entire system to the skin, but is also responsible for the releasing of the drug. The adhesive layer is surrounded by a temporary liner and a backing. It is characterized by the inclusion of the drug directly within the skin-contacting adhesive placed onto the epidermis. Implant 100 may be a Multi-layer Drug-in-Adhesive. The multi-layer drug-in-adhesive patch is similar to the single-layer system; the multi-layer system is different, however, in that it adds another layer of drug-in-adhesive, usually separated by a membrane (but not in all cases). One of the layers is for immediate release of the drug and other layer is for control release of drug from the reservoir. This patch also has a temporary liner-layer and a permanent backing. The drug release from this depends on membrane permeability and diffusion of drug molecules. Implant 100 may be a reservoir type patch. Unlike the single-layer and multi-layer drug-in-adhesive systems, the reservoir transdermal system has a separate drug layer. The drug layer is a liquid compartment containing a drug solution or suspension separated by the adhesive layer. The drug reservoir is totally encapsulated in a shallow compartment molded from a drug-impermeable metallic plastic laminate, with a rate-controlling membrane made of a polymer like vinyl acetate on one surface. This patch is also backed by the backing layer. In this type of system, the rate of release is zero order. Implant 100 may be a matrix type patch. The matrix system has a drug layer of a semisolid matrix containing a drug solution or suspension. The adhesive layer in this patch surrounds the drug layer, partially overlaying it. Also known as a monolithic device. Implant 100 may be a vapor patch. In a vapor patch, the adhesive layer not only serves to adhere the various layers together but also to release vapor.

Still referring to FIG. 1, implant 100 may be a microneedle patch (MNP). A microneedle patch, as used in this disclosure, is a transdermal patch including microneedles as the drug delivery system. For example, implant 100 may be a dissolvable MNP, solid non-soluble MNP, and/or a hollow MNP. In some embodiments, implant 100 may be topical: powder, lotion liniment, solution, emulsion, suspension, ointment, cream, liquid, pastes, gel, and/or suppository. In some embodiments, implant 100 may be in the form of digestible tablets. In some embodiments, implant 100 may be a polymeric drug delivery system, which as used in the disclosure, is a formulation or a device that enables the introduction of a therapeutic substance into the body. For example, implant 100 may a polymeric vaginal ring.

Still referring to FIG. 1, "cardiovascular diseases (CVDs)," as used in this disclosure, are a group of disorders of the heart and blood vessels. It includes: coronary heart disease—a disease of the blood vessels supplying the heart muscle; cerebrovascular disease—a disease of the blood vessels supplying the brain; peripheral arterial disease—a disease of blood vessels supplying the arms and legs; rheumatic heart disease—damage to the heart muscle and heart valves from rheumatic fever, caused by streptococcal bacteria; congenital heart disease—birth defects that affect the normal development and functioning of the heart caused by malformations of the heart structure from birth; and deep vein thrombosis and pulmonary embolism—blood clots in the leg veins, which can dislodge and move to the heart and lungs. Lower levels of estrogen can affect the muscles lining the arteries and can increase the buildup of cholesterol in the arteries. These factors increase a person's risk of atherosclerosis (hardening of the arteries). "Hypothyroidism," as used in this disclosure, is a common condition where the thyroid does not create and release enough thyroid hormone into one's bloodstream. This makes one's metabolism slow down. Also called underactive thyroid, hypothyroidism can make one feel tired, gain weight and be unable to tolerate cold temperatures. "Osteoporosis," as used in this disclosure, is a disease that thins and weakens the bones. Bones become fragile and fracture (break) easily, especially the bones in the hip, spine, and wrist. The hormone estrogen helps keep bones strong. "Anxiety," as used in this disclosure, is a mental health disorder characterized by feelings of worry, anxiety, or fear that are strong enough to interfere with one's daily activities. The reduction, continued deficit, and or changes in levels of estrogens throughout the menstrual cycle are correlated with mood-related distress. "Menopause," as used in this disclosure, is the ceasing of menstruation. Common symptoms include hot flashes and vaginal dryness. There may also be sleep disturbances. The combination of these symptoms can cause anxiety or depression. Estrogen in combination with progesterone and testosterone, promote growth and maintenance of reproductive organs and keeps the vagina moisturized, elastic (stretchy), and well supplied with blood. When in decline of these hormone, menopause may occur.

Still referring to FIG. 1, to combat ovarian decline, implant 100 includes at least an engineered ovarian support cell. An "engineered ovarian support cell," as used in this disclosure, is a reproductive cell originating in an ovary engineered in vitro. "Engineering," as used in this disclosure, is a process that alters the genetic makeup of an organism. Engineering may include altering the DNA makeup such as for example by changing a single base pair, deleting a region of DNA, adding a new segment of DNA, manipulating DNA, modifying DNA, recombining DNA and/or a nucleic acid, and the like. Engineering may include the design and construction of new biological entities such as with the use of laboratory technologies such as enzymes, genetic circuits, and cells or the redesign of existing biological systems. Engineering may include differentiating an engineered ovarian support cell to express one or more transcription factors. A "transcription factor," as used in this disclosure is any protein that controls a rate of transcription. For example, a transcription factor may be selected from NR5A1 and a RUNX family protein. For instance, an engineered ovarian support cell may include an engineered granulosa cell configured to express and/or overexpress NR5A1. An engineered ovarian support cell may express a particular protein and/or transcription factor if a level of the protein is detectable such as for example using a known protein assay. An engineered ovarian support cell may overexpress a particular protein and/or transcription factor if a particular protein and/or transcription factor level is detectable at a higher reference range. For example, an engineered ovarian support cell may overexpress a particular protein if the protein is detectable at a level that is 5% higher than the level of the protein expressed from an endogenous naturally occurring polynucleotide encoding the protein. Engineering may include engineering one or more polynucleotides of an engineered ovarian support cell. An "engineered polynucleotide," as used in this disclosure, is a nucleic acid that does not occur in nature. An engineered polynucleotide may include a recombinant nucleic acid. A "recombinant nucleic acid," as used in this disclosure, is a molecule that is constructed by joining nucleic acids from two different organisms. For example, a recombinant nucleic acid may be created from a human and a mouse. An engineered polynucleotide may include a synthetic nucleic acid. A "synthetic nucleic acid," as used in this disclosure, is a molecule that is amplified and/or chemically synthesized. For example, a synthetic nucleic acid may include a chemically modified and/or otherwise modified nucleic acid that can bind to one or more naturally occurring molecules. An engineered polynucleotide may include DNA (genomic DNA, cDNA, and/or any combination thereof), RNA, and/or a hybrid molecule. An engineered polynucleotide may include complementary DNA which may be synthesized from a single stranded RNA (messenger RNA (mRNA) or microRNA (miRNA)) such as for example using a catalyst such as but not limited to reverse transcriptase. In an embodiment, an engineered polynucleotide may include a promoter operably linked to an open reading frame. A "promoter," as used in this disclosure, is a nucleotide sequence to which RNA polymerase binds to initiate transcription. A promoter may include an inducible promoter. An inducible promoter may be regulated in vitro by a stimulus such as a chemical agent, temperature, or light. This may allow for temporal and/or spatial control of gene expression. For example, an inducible promoter may include but is not limited to an alcohol regulated promoter, a tetracycline operator sequence, a steroid regulated promoter, a human estrogen receptor, and the like. In an embodiment, engineering may include altering of the cell's ability to express, overexpress and/or secrete a hormone including but not limited to hormones such as estrogen, progesterone, testosterone, DHEA and the like. An engineered ovarian support cell may include but is not limited to an engineered granulosa cell, an engineered lutein cell, and/or an engineered theca cell as described below in more detail. In an embodiment, an engineered ovarian support cell may be sourced from an oocyte, granulosa cell, cumulus oocyte complex, and similar cells originating in the ovary. An "oocyte," as used in this disclosure, is a female gametocyte or germ cell involved in reproduction. In an embodiment, an engineered ovarian support cell may include an engineered granulosa cell. A "granulosa cell" is an estrogen-secreting cell of the epithelial lining of a graafian follicle and/or or its follicular precursor. Engineering may include any engineering process as described herein. For instance, and without limitation, a granulosa cell may be engineered to overexpress quantities of estradiol. "Estrogen" as used in this disclosure is a steroid hormone that promotes the development and/or maintenance of female sex characteristics. Estrogen may include but is not limited to estrone (E1), estradiol (E2), Estriol (E3), Esterol (E4) and/or any combination thereof. A "cumulus oocyte complex," as used in this disclosure, is an oocyte containing one or more surrounding cumulus cells. A COC may contain an immature oocyte. A COC may contain a mature oocyte. A "mature oocyte" as used in this disclosure, is one or more mature reproductive cells originating in the ovaries. In some embodiments, engineered ovarian support cell 104 may include but is not limited to an engineered cell and/or any combination thereof including oogonia cells, oogonia-like pluripotent stem cells, polynucleotides, primordial germ cells, and primordial germ cell-like pluripotent stem cells. For example, engineered ovarian support cell 104 may include a pluripotent stem cell (PSC) incorporating: an engineered polynucleotide including an open reading frame encoding a protein selected from Zinc Finger Protein 281 (ZNF281), LIM Homeobox 8 (LHX8), and Spermatogenesis and Oogenesis Specific Basic Helix-Loop-Helix 1 (SOHLH1). In yet another non-limiting example, engineered ovarian support cell 104 may include a pluripotent stem cell (PSC) incorporating an engineered polynucleotide including an open reading frame encoding a protein selected from Distal-Less Homeobox 5 (DLX5), Hematopoietically-expressed homeobox protein (HHEX), and Folliculogenesis Specific BHLH Transcription Factor (FIGLA). In yet another non-limiting example, engineered ovarian support cell 104 may include a pluripotent stem cell (PSC) incorporating an engineered polynucleotide including an open reading frame encoding a protein selected from nuclear receptor subfamily 5 group A member 1 (NR5A1) and a Runt-related transcription factor (RUNX) family protein.

Still referring to FIG. 1, in an embodiment, an ovarian cell may be engineered using Clustered Regularly Interspaced Short Palindromic Repeats (CRISPR) technology. "CRISPR" is programmable technology that targets specific stretches of genetic code to edit DNA at precise locations. CRISPR technology may include CRISPR-CAS 9. Cas9 (or "CRISPR-associated protein 9") is an enzyme that uses CRISPR sequences as a guide to recognize and cleave specific strands of DNA that are complementary to the CRISPR sequence. Cas9 enzymes together with CRISPR sequences form the basis of a technology known as CRISPR-Cas9 that can be used to edit genes within organisms. CRISPR technology may include Class 1 CRISPR systems including type I (cas3), type III (cas10), and type IV and 12 subtypes. CRISPR technology may include Class 2 CRISPR systems including type II (cas9), type V (cas12), type VI (cas13), and 9 subtypes. In some embodiments, CRISPR technology may involve CRISPR-Cas design tools which are computer software platforms and bioinformatics tools used to facilitate the design of guide RNAs (gRNAs) for use with the CRISPR/Cas gene editing system. For example, CRISPR-Cas design tools may include: CRISP-Ron, CRISPRoff, Invitrogen TrueDesign Genome Editor, Breaking-Cas, Cas-OFFinder, CASTING, CRISPy, CCTop, CHOPCHOP, CRISPOR, sgRNA Designer, Synthego Design Tool, and the like. CRISPR technology may also be used as a diagnostic tool. For example, CRISPR-based diagnostics may be coupled to enzymatic processes, such as SHERLOCK-based Profiling of IN vitro Transcription (SPRINT). SPRINT can be used to detect a variety of substances, such as metabolites in patient samples or contaminants in environmental samples, with high throughput or with portable point-of-care devices.

Still referring to FIG. 1, in some embodiments, engineered ovarian support cell 104 may be derived from a pluripotent stem cell. "Pluripotent stem cells," as used in this disclosure, are cells that are able to self-renew by dividing and developing into the three primary groups of cells that make up a human body, including ectoderm, giving rise to the skin and nervous system; endoderm, forming the gastrointestinal and respiratory tracts, endocrine glands, liver, and pancreas; and mesoderm, forming bone, cartilage, most of the circulatory system, muscles, connective tissue, and more. Pluripotent stem cells may be able to make cells from all three of these basic body layers, so they can potentially produce any cell or tissue the body needs to repair itself. Pluripotent stem cells may include induced pluripotent stem cells (iPSCs), which are derived from skin or blood cells that have been reprogrammed back into an embryonic-like pluripotent state that may enable the development of an unlimited source of any type of human cell needed for therapeutic purposes. For example, iPSC can be prodded into becoming beta islet cells to treat diabetes, blood cells to create new blood free of cancer cells for a leukemia patient, or neurons to treat neurological disorders. Induced pluripotent cells may be derived from embryos, embryonic stem cells made by somatic cell nuclear transfer (ntESCs) and/or an embryonic stem cell from an unfertilized egg. In an embodiment, a pluripotent cell may include a human pluripotent cell. In an embodiment, a pluripotent cell may include an embryonic stem cell, such as a human embryonic stem cell. An "embryonic stem cell," as used in this disclosure, is a pluripotent stem cell made using embryos or eggs. An embryonic stem cell may include but is not limited to a true embryonic stem cell, a nuclear transfer embryonic stem cell, and/or a parthenogenetic embryonic stem cell. In an embodiment, a pluripotent stem cell may include an induced pluripotent stem cell such as a human induced pluripotent stem cell. A human induced pluripotent stem cell may be derived from skin or blood cells that may be engineered back into an embryonic-like pluripotent state that enables the development of an unlimited source of any type of human cell.

Still referring to FIG. 1, in some embodiments, engineered ovarian support cell 104 may include an engineered a theca cell. A "theca cell," as used in this disclosure, is one or more endocrine cells associated with ovarian follicles that produce androgens. Engineering may include any engineering process as described herein. An engineered theca cell may be engineered to produce an androgen substrate required for ovarian estrogen biosynthesis, provide signal transduction between granulosa cells and oocytes, provide nutrients, provide structure and support for a follicle as it matures and the like. Theca cells respond to luteinizing hormone (LH) and produce androgens, as well as progesterone in the pre-ovulatory large follicles. An "androgen," as used in this is any natural or synthetic steroid hormone that regulates the development and maintenance of male characteristics in vertebrates by binding to androgen receptors. For example, an androgen may include testosterone, dehydroepiandrosterone (DHEA), androstenedione, dehydroepiandrosterone sulfate (DHEA-5), and/or dihydrotestosterone. Androgens are synthesized in the testes, the ovaries, and the adrenal glands. Androgens in females may serve one or more functions including aiding libido and sexual arousal. Androgens have potential roles in relaxation of the myometrium via non-genomic, androgen receptor-independent pathways, preventing premature uterine contractions in pregnancy. Also, androgens are the precursors to estrogens in both men and women. In addition to their role as natural hormones, androgens are used as medications in hormone replacement therapy. Low androgen levels relating to ovarian decline produce effects such as low libido (interest in or desire for sex), fatigue, decreased sense of well-being and increased susceptibility to bone loss, osteoporosis, and fractures. “Progesterone,” as used in this disclosure, is a steroid hormone belonging to a class of hormones called progestogens. Progesterone prepares the endometrium for the potential of pregnancy after ovulation. It triggers the lining to thicken to accept a fertilized egg. It also prohibits the muscle contractions in the uterus that would cause the body to reject an egg. Low levels of progesterone, in relation to ovarian decline, may cause abnormal menstrual cycles or infertility because the progesterone does not trigger the proper environment for a conceived egg to grow.

Still referring to FIG. 1, in some embodiments, the engineered cell may be a lutein cell. A “lutein cell,” as used in this disclosure, is a cell of the corpus luteum. Engineering may include any engineering process as described herein. An engineered lutein cell may contain lipid droplets and may be derived from granulosa cells and/or the cells of the theca interna. An engineered lutein cell may be engineered to produce and/or secrete predetermined levels of one or more hormones such as progesterone, estrogen, and/or inhibin. “Estrogen,” as used in this disclosure, is a category of sex hormone responsible for the development and regulation of the female reproductive system and secondary sex characteristics Estrogens are responsible for maturation and maintenance of the vagina and uterus, and are also involved in ovarian function, such as maturation of ovarian follicles. In addition, estrogens play an important role in regulation of gonadotropin secretion. For these reasons, estrogens are required for female fertility. Sudden estrogen withdrawal, fluctuating estrogen, and periods of sustained low estrogen levels correlate with significant mood lowering. Estrogens are involved in libido (sex drive) in both women and men. Low levels of estrogen, in relation to ovarian decline, may additionally cause menstrual periods that are less frequent or that stop, hot flashes (suddenly feeling very warm) and/or night sweats, trouble sleeping, dryness and thinning of the vagina, low sexual desire, mood swings, dry skin, weight gain, mainly in your waist, hips, and thighs, menstrual problems, such as light or heavy bleeding, worsening of premenstrual syndrome, fibrocystic breasts (non-cancerous breast lumps), fibroids (noncancerous tumors) in the uterus, fatigue loss of sex drive, depression, osteoporosis, anxiety, and similar conditions.

Still referring to FIG. 1, there are three major endogenous estrogens that have estrogenic hormonal activity: estrone (E1), estradiol (E2), and estriol (E3). Estrone is a steroid, a weak estrogen, and a minor female sex hormone. Estrone, as well as the other estrogens, are synthesized from cholesterol and secreted mainly from the gonads, though they can also be formed from adrenal androgens in adipose tissue. Relative to estradiol, both estrone and estriol have far weaker activity than estrogens. Estrone can be converted into estradiol and serves mainly as a precursor or metabolic intermediate of estradiol. It is both a precursor and metabolite of estradiol. Estradiol is the most potent and prevalent. It can treat symptoms caused by menopause or removal of the ovaries. It can also treat prostate and breast cancer and prevent osteoporosis. Estradiol is responsible for the development of female secondary sexual characteristics such as the breasts, widening of the hips and a female-associated pattern of fat distribution. It is also important in the development and maintenance of female reproductive tissues such as the mammary glands, uterus and vagina during puberty, adulthood, and pregnancy. In the female, estradiol acts as a growth hormone for tissue of the reproductive organs, supporting the lining of the vagina, the cervical glands, the endometrium, and the lining of the fallopian tubes. It enhances growth of the myometrium. Estradiol appears necessary to maintain oocytes in the ovary. During the menstrual cycle, estradiol produced by the growing follicles triggers, via a positive feedback system, the hypothalamic-pituitary events that lead to the luteinizing hormone surge, inducing ovulation. In the luteal phase, estradiol, in conjunction with progesterone, prepares the endometrium for implantation.

Still referring to FIG. 1, estriol is a steroid, a weak estrogen, and a minor female sex hormone. Levels of estriol in women who are not pregnant are almost undetectable. However, during pregnancy, estriol is synthesized in very high quantities by the placenta and is the most produced estrogen in the body by far, although circulating levels of estriol are similar to those of other estrogens due to a relatively high rate of metabolism and excretion. “Inhibin,” as used in this disclosure, is a protein secreted that obstructs the synthesis and release of the follicle-stimulating hormone (FSH) in the pituitary gland and reduces the hypothalamic luteinizing hormone (LH)—releasing hormone content. In relation to ovarian decline, aging woman may have increased FSH levels during the follicular phase despite normal estrogen and LH levels and regular menstrual cycles. This FSH rise occurs some years before menopause and accompanies the decline of ovarian follicular reserve and fertility rate. The selective FSH rise of late reproductive years might be a consequence of declining inhibin secretion by a reduced pool of ovarian follicles.

Still referring to FIG. 1, in some embodiments, an engineered ovarian support cell may be a follicle-stimulating hormone (FSH) responsive cell. For example, an iPSC-derived (induced pluripotent stem cell derived) granulosa cell capable of producing all hormones herein disclosed, that is steroidogenic when FSH is present at physiologically relevant levels, and non-steroidogenic when it is not, as described further below. “Steroidogenic,” as used in this disclosure are cells that are involved in steroidogenesis and steroid biosynthesis. They are responsible for the biosynthesis of the steroid hormones, including sex steroids (androgens, estrogens, and progestogens) and corticosteroids (glucocorticoids and mineralocorticoids), as well as neurosteroids, from cholesterol. Steroidogenic cells are most highly expressed in classical steroidogenic tissues, such as the testis, ovary, and adrenal cortex, but are also present in other tissues in the body. The engineered ovarian support cell may produce activins, Anti-Müllerian hormone (AMH), and Epidermal growth factor (EGF). “Activins,” as used in this disclosure, are dimeric proteins composed of βA- and βA-subunits (activin A), βB- and βB-subunits (activin B), or βA- and βB-subunits (activin AB). Activins stimulate FSH synthesis and secretion. “Anti-Müllerian hormone,” as used in this disclosure, is a glycoprotein hormone structurally related to inhibin and activin from the transforming growth factor beta superfamily, whose key roles are in growth differentiation and folliculogenesis. AMH is expressed by granulosa cells of the ovary during the reproductive years and limits the formation of primary follicles by inhibiting excessive follicular recruitment by FSH. AMH expression is greatest in the recruitment stage of folliculogenesis, in the preantral and small antral follicles. This expression diminishes as follicles develop and enter selection stage, upon which FSH expression increases. Some authorities suggest it is a measure of certain aspects of ovarian function, useful in assessing conditions such as polycystic ovary syndrome and premature ovarian failure. "Epidermal growth factor," as used in this disclosure, is a protein that stimulates cell growth and differentiation by binding to its receptor, epidermal growth factor receptor. EGF may be used to modify synthetic scaffolds for manufacturing of bioengineered grafts by emulsion electrospinning or surface modification methods.

Still referring to FIG. 1, engineered ovarian support cell 104 may, in response to a physiological conversation between a user's brain and the user's ovary, secrete key ovarian hormones and provide personalized hormone delivery in real-time as described further below. A "user," as used in this disclosure is a living organism such as a human being, plant, animal, and all other organisms composed of cells. For example, a user may be a human patient experiencing ovarian decline. The feedback interaction between engineered ovarian support cell 104 and a patient's hormonal environment may mimic pre-menopausal brain signaling relating to the production and release of hormones in the body. A "hormonal environment," as used in this disclosure are areas in the human body prone to hormone signaling and interaction. The hormonal environment may be the endocrine system in the body, the brain, blood stream, and the like. For example, steroidogenic cells form a mural granulosa group responding to FSH, while the mixed population (with more of a cumulus identity) may provide the cell-to-cell mechanical environment and response to estradiol (E2) (such as AMH production and human chorionic gonadotropin (hCG) trigger response).

Still referring to FIG. 1, engineered ovarian support cell 104 may be configured to secrete a hormone in a cyclic dose. A "cyclic dose," as used in this disclosure, is a hormone dose that is administered in a cyclical pattern. A "cyclical pattern," as used in this disclosure is the level and type of hormone secreted in response to a user's brain signaling for production and release of the hormone as described further below. For example, lutein cells may secrete progesterone. Granulosa cells may secrete estrogen. Theca cells may secrete androgens such as testosterone. The levels and specific secretions of engineered ovarian support cell 104 fluctuate over time and in response to signals from the brain and environment and are unique to each individual user unlike in continuous dosing methods in hormone replacement therapy. Continuous dosing involves a fixed does of a substance being administered to user, not tailored to the physiological relationship between the brain and the ovary which is not how hormones are naturally delivered in the body. Even with precise dose calculators it may be impossible to calculate the ever-fluctuating hormonal requirements of user. What cyclical pattern dosing does is integrate into chemical conversation, respond to signals from brain and ovaries, and tunes levels of hormones released to each individual woman's system. This real time feedback avoids the limitations and side effects of continuous systemic hormonal administration and is essential to prevent the downstream consequences of ovarian decline. Female reproduction relies on a complex balance of hormones that drive the reproductive cycle (menstrual cycle in humans) and influence fertility. A hormone called GnRH, which stands for gonadotropin-releasing hormone, plays a major role in regulating this balance. GnRH is transmitted from the brain and stimulates the release of other hormones from a nearby gland called the pituitary gland, which, in turn, activates the reproductive organs to produce steroid hormones, such as estrogen.

Still referring to FIG. 1, steroids do many things in the body, including regulating the release of GnRH and pituitary hormones through a process called feedback. A "feedback" mechanism, as used in this disclosure, is a loop in which a product feeds back to control its own production. In the case of negative feedback, steroids maintain the release of GnRH and pituitary hormone within a normal range. Once per reproductive cycle, estrogen will instead positively feed back into the system and activate GnRH, causing pituitary hormone levels to spike, and initiate the release of one or more eggs from the ovary by a process known as ovulation. The neurons that make GnRH do not directly respond to estrogen, but instead receive input from different upstream neurons that contain estrogen receptors. For example, treating menopausal symptoms with estrogen and progestin together is known as estrogen-progestin therapy (EPT) or combined hormone therapy. Although estrogen alone improves the symptoms of menopause, it increases the risk of cancer of the uterus (endometrial cancer). Adding a progestin to the estrogen lowers the risk of endometrial cancer back to normal. Because of this, EPT is given to women who still have a uterus (those who have not had a hysterectomy). EPT can be given in 2 ways: continuous EPT means the same dose of estrogen and progestin is taken each day. Women often prefer continuous EPT because it rarely leads to menstrual-like bleeding. Sequential (cyclical) EPT means different amounts of each hormone are taken on specific days. There are different ways to do this. For example, estrogen can be taken by itself for 14 days, then estrogen plus progestin for 11 days, then neither hormone for 3 to 5 days. However, these methods do not allow for real time feedback to administer hormones exactly based on brain signaling. EPT is linked to a higher risk of breast cancer. The longer EPT is used, the higher the risk. In women who still have a uterus, using systemic estrogen therapy has been shown to increase the risk of endometrial cancer (cancer of the lining of the uterus). Therefore, because implant 200 implements cyclic dosing there is a lower chance of cancer risks and other side effects related to HRT since the natural hormones released from the brain will drive the membrane response hormone secretion in the exact way that the brain-ovarian axis is designed, instead of prolonged administration of fixed hormone levels that may be become detrimental to the user in the long term.

Still referring to FIG. 1, With over 1 billion women experiencing menopause today, it is a huge, but underserved market. Estimates suggest that women in menopause spend an average of $2,000 a year on prescriptions, doctor visits, treatments, devices, and products to address symptoms like night sweats, loss of libido, fatigue and difficulty concentrating. Cyclic dosing may be financially advantageous to a user since the dose is personalized and would not require multiple applications, prescriptions, and trials of the average fixed dose hormone products.

Still referring to FIG. 1, implant 100 includes an extracellular matrix substrate 108. In some embodiments, engineered ovarian support cell 104 or a plurality of engineered ovarian support cells 104 may be embedded within extracellular matrix substrate 108, as described further below. “Embed,” as used in this disclosure, is the process of fixing an object in a surrounding mass. For example, embedding may include a cell binding to a collagen receptor in an extracellular matrix. As used in this disclosure, an “extracellular matrix (ECM),” is a non-cellular component that provides physical scaffolding for the cellular constituents and initiates crucial biochemical/biomechanical cues. An “extracellular matrix substrate,” as used in this disclosure, is a network containing one or more extracellular macromolecules and/or minerals that functions to provide structural and/or biochemical support. Extracellular matrix substrate 108 may bind and/or embed one or more ingredients contained within implant 100. Extracellular matrix substrate 108 may include macromolecules and minerals, such as collagen, Epidermal growth factors (EGFs) enzymes, glycoproteins and hydroxyapatite that provide structural and biochemical support to surrounding cells. In some embodiments, an extracellular matrix may include a collagen matrix. An ECM collagen matrix may include a combination of 20 or more different types of collagens. Collagen may include one or more combinations of Types 1-20. Combinations may be based on weight %, quantity of each type used, and the like. For example, collagen I, II, III, V and XI which are fibrillar collagen commonly found in connective tissue, may be used in the ECM, individually or combined. In some embodiments, extracellular matrix substrate 108 may include an elastin. Elastin is hydrophobic protein of 750 amino acids, rich in proline and glycine. Tropoelastin, a soluble precursor secreted into the extracellular space assembles into insoluble elastic fibers and sheets. Elastic fibers provide required resilience so that tissues can recoil after transient stretch. In some embodiments, extracellular matrix substrate 108 may include a fibronectin. Fibronectin is a large glycoprotein (220 kDa) composed of two polypeptide chains (dimer) joined by disulfide bonds at one end. Each polypeptide is further folded into functionally and structurally distinct domains which bind to various components of ECM (glycosaminoglycans, proteoglycans, and collagen) and cell surface proteins. Fibronectin is secreted by wide variety of connective tissue cells, including fibroblasts, chondrocytes, schwann cells, macrophages, intestinal epithelial cells and hepatocytes. Fibronectin is a multifunctional protein involved in cell adhesion and spreading. It also regulates cellular morphology, cell migration, cytoskeletal organization, hemostasis and wound repair.

Still referring to FIG. 1, extracellular matrix substrate 108 may include a laminin. Laminin is major component of basal lamina. It is composed of three long polypeptide chains (designated α, β, and γ) held together by disulfide bonds and arranged in asymmetric cross shape. Laminin acts as glue, which holds cells and the ECM together. It has active domains for collagen binding, cell adhesion, heparin binding and neurite outgrowth fragment. Laminins modulate cell growth, motility and signaling pathways. In some embodiments, extracellular matrix substrate 108 may include vitronectin. Vitronectin is glycoprotein of 459 amino acids, found in ECM and blood. It circulates in blood either in the form of single chain moiety of 75 kDa or as two chain moieties of 65 kDa and 10 kDa. Vitronectin interacts with polysaccharides (Glycosaminoglycans) and proteoglycans, acting as cell adhesion molecule. Although vitronectin and fibronectin have similar functions and have an Arg-Gly-Asp cell recognition sequence, they are structurally and immunologically distinct. Vitronectin acts as inhibitor of cytolytic complement pathway and have physiological role in coagulation pathway. In addition, it promotes cell migration, proliferation, differentiation and spreading of endothelial and neoplastic cell. Other embodiments of extracellular matrix substrate 108 may include alginate, proteoglycans, heparan sulfate, chondroitin sulfate, keratan sulfate, hyaluronic acid, elastin, fibronectin, dermatan sulfate, collagen, extracellular vesicles, nanoparticles, microparticles, proteins, cell adhesion proteins, proteoglycans, carbohydrate polymers, non-proteoglycan polysaccharides, any combination thereof, and other forms of substrates one skilled in the art may understand as applicable.

Still referring to FIG. 1, the ECM may be a collagen polymer matrix is about 100-500 micron particles. A “collagen polymer matrix,” as used in this disclosure, is a matrix composed of collagen-based macromolecules. A collagen polymer matrix may include collagen types 1-20 as described above individually or in combination. For example, the collagen polymer matrix may be a collagen type III biopolymer matrix derived from fetal, neo-natal and/or post-natal animal tissue. As used in this disclosure, “micron particles,” (microparticles) are spherical particles between 0.1 and 100 μm in size. containing a core substance enclosed by one or more membranes or shells. Microparticles may be further classified as microspheres and microcapsules based on their internal structure. Microspheres are generally formed by a homogeneous matrix in which it is not possible to separate a core and a membrane, while the drug is dispersed in the polymer matrix either as small clusters or molecularly. Microcapsules are formulations constituted by a central liquid, solid, or semisolid core containing the drug, alone, or in combination with excipients, surrounded by a membrane or a continuous polymer coating. Commercially available microparticles are available in a wide variety of materials, including ceramics, glass, polymers, and metals. Microparticles offer various significant advantages as drug delivery systems, including: (i) an effective protection of the encapsulated active agent against (e.g. enzymatic) degradation, (ii) the possibility to accurately control the release rate of the incorporated drug over periods of hours to months, (iii) an easy administration (compared to alternative parenteral controlled release dosage forms, such as macro-sized implants), and (iv) Desired, pre-programmed drug release profiles can be provided which match the therapeutic needs of the patient. In some embodiments, the ECM may contain Poly (lactic acid) (PLA), and/or poly (lactic-co-glycolic acid) (PLGA), microparticles. In some embodiments, the ECM may be a collagen polymer matrix about 500-800 micron cubes. As used in this disclosure, a “micron cube,” is a derived metric SI (System International) measurement unit of volume with sides equal to one micron (1 μm). Additionally, or alternatively, the ECM may be perforated.

Still referring to FIG. 1, implant 100 includes a delivery apparatus. A “delivery apparatus,” as used in this disclosure is a device utilized to deliver a substance to a living being. A “substance” as used in this disclosure includes any substance as described above in more detail. A substance may include an engineered ovarian support cell. A substance may include a drug product. A substance may include a vitamin, supplement, hormone, and the like. A delivery apparatus may be biocompatible with a living being. “Biocompatible,” as used in this disclosure, is the ability of implant 100 to be compatible with a living being while implant 100 is in contact with the living being. Contact may include for example when implant 100 is administered and/or inserted into a living being. For example, implant 100 may be sub-dermally inserted into a human being’s arm where it may be biocompatible with the human being. In an embodiment, implant 100 may be biocompatible with a living being for a certain period of time such as 3 months and/or 3 years. After the expiration of a certain period of time implant 100 may have to be removed. In an embodiment, delivery apparatus may be composed of, a biocompatible material such as synthetic polymers (water repelling materials like α-hydroxy acid [it is a family which consists of poly(lactic-co-glycolic) acid, PLGA], polyanhydrides, etc.), naturally occurring polymers (Polyvinylchloride (PVC), Polyethylene (PE), Polypropylene (PP), Polymethyl methacrylate (PMMA), Polystyrene (PS), Polytetrafluoroethylene (PTFE), Polyurethane (PU) and Polyamide (nylon), Polyethylene terephthalate (PET), Polyether sulfone (PES), etc.), composite material (plastic fiberglass, bone, etc.), ceramic material (lumina(Al2O3), Zirconia (ZrO2) (bioinert), Bioglass (Na2OCaOP2O3-SiO), etc.), and the like. In some embodiments, delivery apparatus 112 may be a hard biocompatible rod made of plastic or silicone. In some embodiments, the delivery apparatus may include an ECM.

Still referring to FIG. 1, in some embodiments, delivery apparatus 112 may include a subdermal rod. A "subdermal rod," as used in this disclosure, is biocompatible material of such small dimensions that it can be fitted subcutaneously with at least an ordinary hypodermic needle. In some embodiments, the subdermal rod may be modeled after FDA-approved contraceptive devices, such subdermal implants Implanon and Nexplanon as produced by Merk, headquartered in Readington Township, NJ; Jadelle as produced by Bayer OY, headquartered in Finland; Vivelle Patch as produced by Novartis AG, headquartered in Basel, Switzerland; Alora patch as produced by Allergan, headquartered in Dublin, Ireland; Climara Patch as produced by Bayer, headquartered in Leverkusen, Germany; Delestrogen injection as produced by Par Sterile Products LLC, headquartered in Chestnut Ridge, N.Y.; Esclim patch as produced by Fournier Research, Inc., headquartered in New Jersey, United States; Estraderm patch as produced by Novartis, headquartered in Basel, Switzerland; Evamist skin spray as produced by KV Pharmaceutical, headquartered in St. Louis, MO; Femring as produced by Millicent Pharma, headquartered in East Hanover, NJ; Menostart patch as produced by Bayer; Minivelle patch as produced by Noven Pharmaceuticals, headquartered in Miami, Florida; and Vivelle-Dot patch as produced by Novartis. For example, the subdermal rod may plastic rod including and ethylene vinylacetate (EVA) copolymer core, containing 68 mg of the engineered ovarian cell, surrounded by an EVA copolymer skin. In some embodiments, the subdermal rod may be cylindrical or virtually cylindrical with a section of ranging between 1.5 and 2.0 mm, and a length between 1 and 5 cm. For example, the subdermal rod may be a 2" long biocompatible plastic rod made of medical grade PVC. Additionally, the subdermal rod may contain an extracellular matrix encapsulating engineered ovarian support cell 104. For example, the extracellular matrix may be located in the core of the rod. In some embodiments, delivery apparatus 112 may include a membrane 116, micro needle patch, gel, cream, spray and the like. Active ingredients in the subdermal rod may include etonogestre, desogestrel, levonorgestrel, ethinylestradiol, mestranol, quinestrol, ethinylestradiol sulfonate, moxestrol, methylestradiol, estrogen esters, such as estradiol valerate, estradiol cypionate, estradiol acetate, estradiol benzoate, estradiol undecylate, and polyestradiol phosphate, progesterone, progestogen, acetomepregenol, algestone acetophenide, chlormadinone acetate, testosterone, and similar hormone medications. Inactive ingredients may include barium sulfate, magnesium stearate, ethylene-vinyl acetate copolymer, and other material described through this disclosure. Benefits of using a subdermal rod in hormone therapy: improved response when other treatments have failed and long-term bone protection, effectiveness in relieving menopausal symptoms in women who only respond to higher doses of HRT or in those who have had a surgical menopause, because the implants achieve higher levels of hormone in the circulation reversibility of long-term effects by removal of the rod. The ability of the rod to be easily removed plays a key role in preventing the long term effect correlated to systemic HRT wherein, medication is secreted and absorbed by the user at a fixed rate. Because the implant utilizes cyclic doing, a user is less likely to grow dependent and when the implant is removed, there may be little to no long-term effects contributed to irreversible or long-term HRT methods.

Still referring to FIG. 1, in some embodiments, implant 100 may include a membrane 116 containing a membrane surrounding delivery apparatus 112 for subdermal implantation of delivery apparatus 112. A "membrane," as used in this disclosure is an outer layer of an object. Membrane 116 may be a selective barrier. For example, membrane 116 include epithelial membranes, serous membranes, connective tissue membranes, synovial membranes, and meninges. In some embodiments, membrane 116 may directly encapsulate an ECM containing engineered ovarian support cell 104 without delivery apparatus 112. To "encapsulate," as used in this disclosure is to enclose a substance. Encapsulation is commonly adopted in drug delivery systems to form a shell to protect a particular drug and prevent it from leaching out before reaching the targeted site. The outer layer may be made of hydrogel matrices or polymeric nanostructures that are able to entrap the targeted drug, as described further below. Membrane 116 may include any extracellular matrix substrate, alone or in combination, as disclosed above. Additionally, extracellular matrix substrate may include any material used in membrane 116 as described throughout this disclosure. In some embodiments, membrane 116 may include polymers as described above. In some embodiments, membrane 116 may include a polymer matrix composite. "Polymer matrix composites (PMCs)," as used in this disclosure, are materials that uses organic polymer as matrix and fiber as reinforcement. There are different types of PMCs according to the polymer types like thermosets and thermoplastic polymers, epoxy, polymers other than epoxy, amorphous and semi crystalline polymers. In some embodiments, membrane 116 may include one or more perforated sheets. A "perforated sheet," as used in this disclosure, is a nanomembrane with one or more openings acting as a passageway. For example, membrane 116 may be a polymer extracellular matrix, wherein the end of the patch is the side to come into direct contact with a user's hormonal environment. Perforated sheets may exhibit one or more qualities such as being freely suspended on the centimeter scale, exhibiting high mechanical strength, containing low surface energies and/or a sharp permeability cutoff at a hydrodynamic diameter of 10 nm suitable for protein separations. Perforated sheet may include any perforated sheet as described below in more detail in reference to FIG. 5.

Still referring to FIG. 1, the pore (perforation) size of membrane 116 may allow for bi-directional flow of small molecules, such as the secreted hormones of engineered ovarian support cell 104, but not migration of cells out of delivery apparatus 112. "Bi-directional flow," as used in this disclosure, is the selective passage of a substance in both directions. A substance may be any substance as described throughout this disclosure, such as estrogen. For example, the pore size may be 25 microns in diameter while the cell is 81 microns. In some embodiments, membrane 116 may be a hard or closed biocompatible plastic or silicone device that keeps the cells encapsulated while allowing communication between engineered ovarian support cell 104 and the patient via the bloodstream. For example, the membrane 116 may act as an ectopic ovarian hub and sit on top of the user's skin. Once in contact with a user's hormonal environment, membrane 116 may allow bidirectional transmission of mechanical and biochemical signals across the patch membrane which may lead to a cooperative regulation of engineered ovarian support cell 104 functions, such as secretion of a hormone. Regarding implantation, when membrane 116 is in contact with the bloodstream, the patch may integrate into the bi-directional signaling of the user's brain and ovaries and only secretes the hormones signaled for production in lieu of the ovaries. In some embodiments, implantation of delivery apparatus 112 is reversible unlike in typical methods of hormone replacement therapy. "Reversible," as used in this disclosure, is the removal of an implant from a user. Reversibility may include the short-term effect and/or half-life of the secreted hormones in a user. Implant 100 may be reversible in a minor procedure so that all cells will remain in the polymer and can be removed if needed (e.g., in the case of estrogen-dependent cancer), in contrast to injected agents which disperse through the patient's system. The fixed does of hormones administered in HRT do not replicate the physiological relationship between the brain the ovaries and may lead to one or more effects due to prolonged use or imbalance of hormones administered. For example, HRT side effects may include breast tenderness, headaches, indigestion, abdominal (tummy) pain, vaginal bleeding, breast cancer (small but increased risk), deep vein thrombosis (small but increased risk), uterine lining growth, which can increase the risk of uterine cancer, Alzheimer's, stroke, heart attack, and similar conditions. Even with the most precise dose calculators, it would be nearly impossible to continuously measure blood markers and lifestyle factors and alter the dose in real-time using current methods of HRT. In addition, the pharmacokinetic properties such as the half-life of one or more hormones delivered via traditional HRT methodologies such as via a transdermal cream may allow hormones to continue to circulate in the body for days after cessation.

Figure 2:
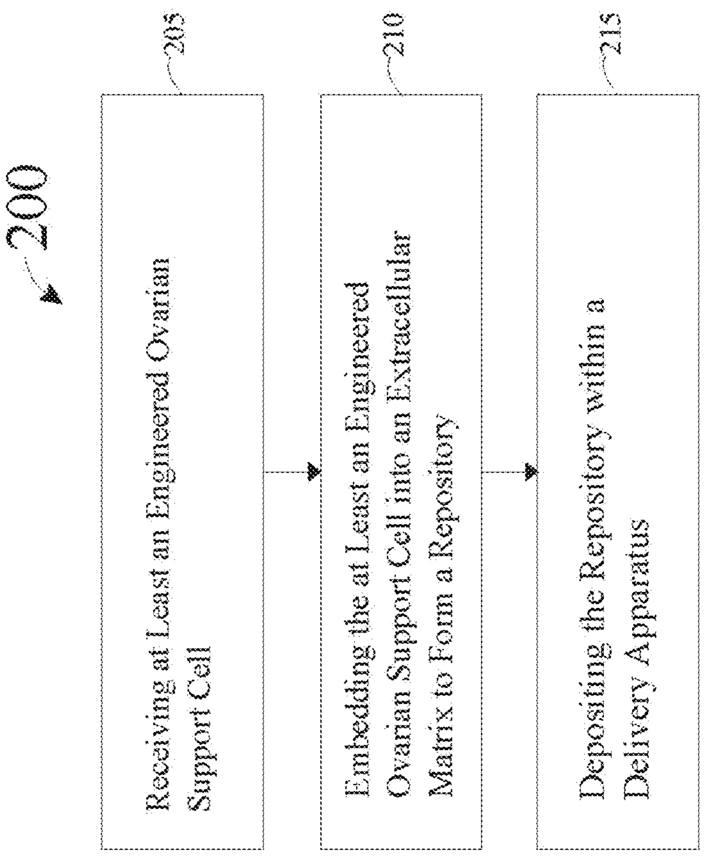
FIG. 2 is an exemplary flow diagram of a method for manufacturing an implant for ovarian decline.

Referring now to FIG. 2, is an exemplary flow diagram of a method 200 for manufacturing an implant 100 for ovarian decline is illustrated. At step 205, method 200 includes receiving at least an engineered ovarian support cell. An engineered ovarian support may be any engineered ovarian support as defined and described in FIG. 1. For example, the engineered ovarian support cell may be a steroidogenic granulosa cell genetically modified and/or altered, using CRISPR technology, to express a certain quantity of hormones and/or a certain type of hormones. Receiving the engineered ovarian support cell may include maturation of an oocyte received to a user in vitro. In some embodiments, receiving the engineered ovarian cell may include donation of an oocyte from a person not related to the user. Ovarian cells may be engineered in vitro using cellular cultivation methods. In some embodiments, engineering and ovarian support cell may involve ovarian cryopreservation has been done for decades, resulting in restoration of hormonal balance. Ovarian cryopreservation involves surgically extracting part of the ovary and freezing the ovarian cell-based tissue patches for reimplantation later in life. The reinsertion of the autologous ovarian patch leads to restoration of hormonal cycles and even spontaneous fertility. Many successful pregnancies have resulted from ovarian cryopreservation. This process is most commonly done to preserve future fertility and hormone production in prepubescent girls undergoing chemotherapy. Studies have found that, of women who have undergone ovarian cryopreservation, 62% conceive spontaneously, 64% have prolonged ovarian endocrine function, and 37% have a live birth.

At step 210, method 200 includes embedding the at least an engineered ovarian support cell into an extracellular matrix to form a repository. A "repository," as used in this disclosure, is a dwelling used to store one or more cells. The repository may be perforated wherein the size of the pores may allow for bi-directional flow of small molecules, such as the secreted hormones of engineered ovarian support cell, but not migration of the engineered cells out of the repositor. In addition, the repository may allow for cyclic secretion of one or more hormones expressed and/or secreted by one or more engineered ovarian support cells. The extracellular matrix may be one as disclosed above, for example and with reference to FIG. 1. Embedding may include cell encapsulation methods such as emulsion, microfluidics, lithography, extrusion, and any other method one skilled in the art may understand as applicable. Encapsulation by emulsion may be performed by dispersing a hydrogel precursor into a non-miscible phase. Surfactants can be used to stabilize the emulsion and to obtain smaller drops (microemulsion). When the dispersion reaches equilibrium, the polymer drops are hardened according to the sol-gel mechanism of the hydrogel. Regarding microfluidics, it is a technique dealing with the handling of fluids in microenvironments, such as microchannels where the flow of fluids is generally laminar. The flow is characterized by low Reynolds numbers, meaning that it is dominated by viscous stresses with negligible inertia effects. The laminar flow allows a fine control over the characteristics of the microdrop. The generation of the microdrops may include the formation of emulsions of the polymer droplets in a non-miscible continuous phase. The generation of individual drops through microfluidics can be seen as a bottom-up approach to emulsification, compared with standard emulsification techniques being the top-down approach. In this bottom-up approach, a suspension of hydrogel precursor and cells is injected into a microchannel and the droplets are formed when the suspension intersects the continuous phase coming from other inlets. The intersection between the channels can have different geometries, with the T-junction and the flow-focusing being the most common.

Still referring to FIG. 2, cell encapsulation may include litography including but not limited to soft lithography and/or photolithography. Soft lithography is a strategy based on self-assembly and replica molding for carrying out micro- and nanofabrication. In this technique, a polymer solution may be poured or spin-coated onto a master and then is cross-linked, obtaining a rubbery replica. The replica may contain channels that can be filled with a suspension of a hydrogel precursor and cells. The channels are usually filled by pressing the replica onto the cell suspension. Regarding Extrusion, method to encapsulate cells into hydrogel beads includes gravitational dripping. A suspension of hydrogel precursor and cells is extruded through a small tube (i.e., a needle), the drop grows and when it reaches a critical mass it freely falls into a suitable hardening bath. This method usually leads to capsules above 1 mm diameter and because of the impact onto the bath they are not always spherical.

Still referring to FIG. 2, at step 215, method 200 includes depositing the repository within a delivery apparatus 112. A delivery apparatus may include any delivery apparatus as described above in more detail in FIG. 1. Deposition may occur by submerging delivery apparatus 112, such as a subdermal rod, into the repository and allowing the delivery apparatus to soak and fill up with the repository. In some embodiments, the repository may be injected into the delivery apparatus using a device such as a syringe.

Figure 3:
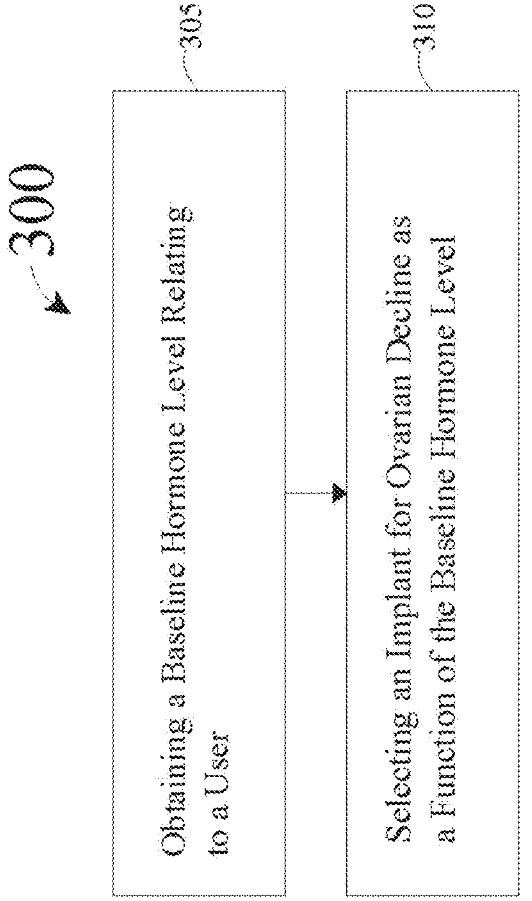
FIG. 3 is an exemplary flow diagram of a method reversing ovarian decline.

Referring now to FIG. 3, is an exemplary flow diagram of a method 300 for reversing ovarian decline is illustrated. At step 305, method 300 includes obtaining a baseline hormone level relating to a user. A "hormone level," as used in this disclosure, is a quantitative value representing a level of one or more hormones of a user. The baseline hormone level may include quantitative values of estradiol (E2), luteinizing hormone (LH), follicle-stimulating hormone (FSH), progesterone (P4), estrone (E1), estriol (E3), testosterone, androgens, dehydroepiandrosterone (DHEA), triiodothyronine (T3), tetraiodothyronine (T4), calcitonin, melatonin, insulin, cortisol, human growth hormone (HGH), adrenaline levels and the like. In some embodiments, the baseline of hormone levels may be based on a blood analysis relating to a user. For example, blood analysis may include plasma hormone analysis techniques. In some embodiments, the baseline of hormone levels may be based on saliva hormone testing techniques. The baseline of hormone levels may be based on other forms of analysis such as hair, urine, and the like. At step 310, method 300 includes selecting an implant 100 for ovarian decline as a function of the baseline hormone level. In some embodiments, implant 100 may include at least an engineered ovarian support cell; an extracellular matrix substrate; and a delivery apparatus, for example and with reference to FIGS. 1 and 2. The implant selected may be an implant including the engineered ovarian cells configured to secrete hormones to replenish low levels of hormones relating to a user relating to the obtained baseline hormone levels. The baseline hormone levels may dictate the quantity and types of engineered ovarian support cells an implant may have to secrete hormone doses to adjust a user's hormone level as needed. The baseline hormone levels may be used to monitor the efficiency of ovarian decline reversal in a patient after implantation.

Figure 4:
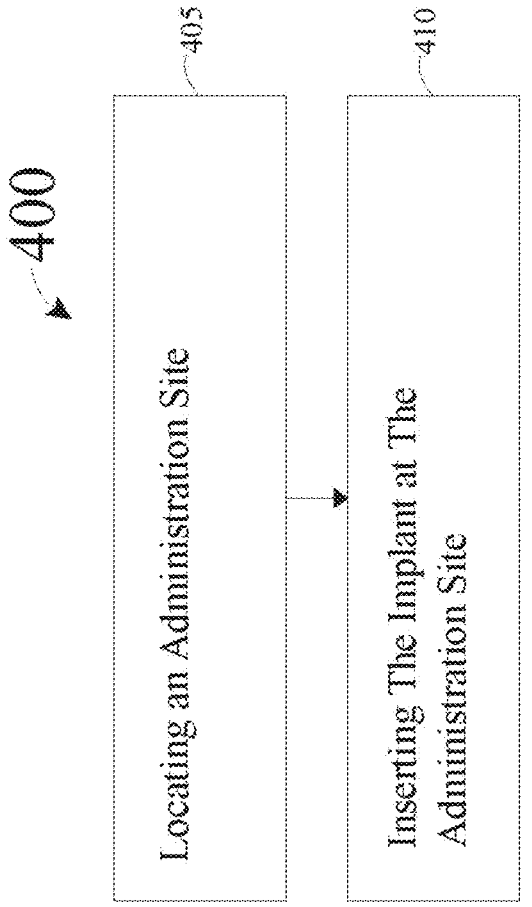
FIG. 4 is an exemplary flow diagram of a method for administering an implant for ovarian decline.

Referring now to FIG. 4, is an exemplary flow diagram of a method 400 for administering an implant for ovarian decline. The implant may be any implant as described throughout this disclosure. For example, the implant may be implant 100 as described in FIG. 1. At step 405, method 400 includes locating an administration site. As used in this disclosure, an "administration site," is the location of application of the implant on a user. For example, the administration site for an IUD Implant may be the uterus. The administration site for a transdermal patch may include but is not limited to the upper chest, upper arm, lower abdomen, or hip of a user. In some embodiments, the implant may be a subdermal rod surrounded by a patch membrane as described in FIG. 1, wherein the administration locating the administration site includes identifying a location to accommodate bi-directional flow from the implant. This may be a site that is close to blood vessels. For example, the administration site may be under the epidermis just above the dermis layer of a user's skin. The epidermis is the thin, outer layer of the skin that is visible to the eye and works to provide protection for the body. This part of the skin does not contain any blood vessels and is, therefore, dependent on the dermis. The epidermis consists of stratified squamous epithelial cells. There are four layers of the epidermis, according to the maturation of the cells: stratum germinativum, stratum spinosum, stratum granulosum, and stratum corneum. The "dermis," as used in this disclosure is the layer of skin that lies beneath the epidermis and above the subcutaneous layer. It is the thickest layer of the skin and is made up of fibrous and elastic tissue. Thus, it provides strength and flexibility to the skin. The dermis includes two layers: the papillary dermis and the reticular dermis. The papillary dermis is the more superficial of the two and lies just beneath the epidermal junction. It is relatively thin and is made up of loose connective tissue, which includes capillaries, elastic fibers, reticular fibers, and collagen, The reticular dermis is the deeper and thicker layer of the dermis, which lies above the subcutaneous layer of the skin. It contains dense connective tissue, which includes blood vessels, elastic fibers (interlaced), collagen fibers (in parallel layers), fibroblasts, mast cells, nerve endings, and lymphatics. Additionally, there is a substance surrounding the components in the dermis. This has a gel-like consistency because it contains mucopolysaccharides, chondroitin sulfates, and glycoproteins. As there is no direct blood supply to the epidermis, this outermost layer of the skin relies on the underlying dermis, for the supply of nutrients and disposal of waste products. This occurs via a process of diffusion through the dermo-epidermal junction, which lies just below the stratum germinativum of the epidermis. An epidermis administration site may allow for bi-directional signaling and transmission of secreted hormones from the implant into the dermis layer containing the bloods vessels, a hormonal environment.

Still referring to FIG. 4, at step 410, method 400 includes inserting the implant at the administration site. In some embodiments, the implant may be inserted sub dermally in the upper arm. To reduce the risk of neural or vascular injury, the implant may be inserted at the inner side of the non-dominant upper arm about 8-10 cm (3-4 inches) above the medial epicondyle of the humerus. Insertion may include using an application such as, a hypodermic needle, vaginal cylinder applicator, ovoid's applicator, and similar devices. In some embodiments, the applicator may be modeled after the implant applicator used in applying Nexplanon and Implanon, respectively. Insertion may follow safety protocols applied by healthcare professionals. For example, confirming medical history of the user, sterilizing and numbing the administration site, and similar steps.

Figure 5:
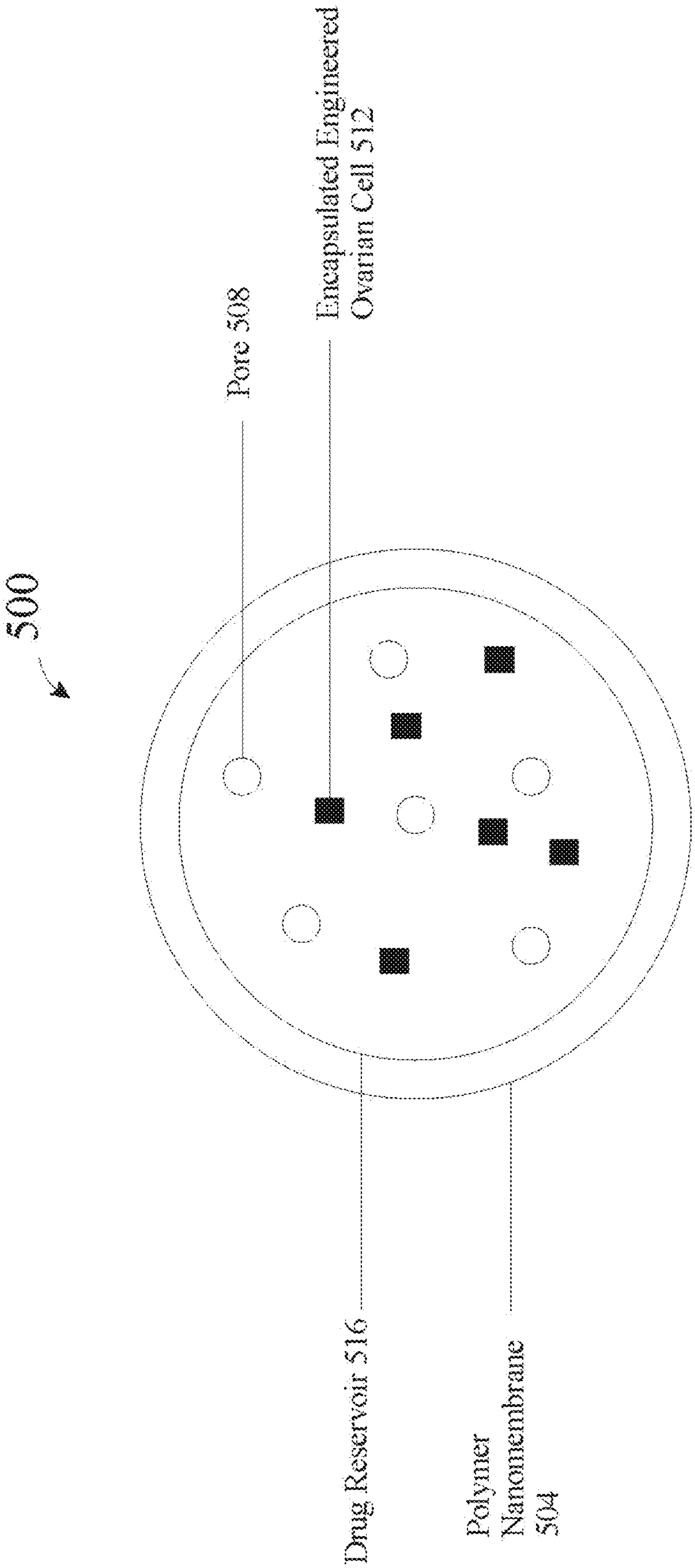
FIG. 5 is an exemplary embodiment of an ECM for encapsulating an engineered ovarian support cell.

Referring now to FIG. 5, is an exemplary embodiment of an ECM for encapsulating the engineered ovarian support cell. ECM may be a polymer nanomembrane 504. Polymer nanomembranes 504 are synthetic structures with thickness less than 100 nm. Nanomembranes may be made from polymers such as Polyacrylonitrile (PAN), Polyethylene (PE), Polyvinylidene Fluoride (PVDF), polyamide, Polypropylene, and polyether sulfone (PES). Their surface-area-volume ratio increases to at least a few orders of magnitude. These membranes have pore size in the range of 1 nm to 300 nm. Nanomembranes allow for regulation of the physio-chemical properties of membrane pores 508, which make them attractive for controlling drug delivery rates. Membranes are used to control the rate of delivery of drugs to the body as well as drug permeation from the reservoir to attain the required rate of drug delivery. Therefore, drug delivery is controlled by both passive diffusion and biodegradation mechanisms. Membranes can carry one or more bioactive agents and have been developed into different classes of carriers. These different carriers can be carbon-based nanomaterials, polymeric membranes, and inorganic membranes, where the bulk properties of the membrane are governed by its building blocks, i.e., the nanoparticles. As used in this disclosure, a "drug encapsulated engineered ovarian cell" is an engineered ovarian support cell encapsulated by a membrane and/matrix. Here, a drug encapsulated engineered ovarian cell 512 may be held in the compartment of a drug reservoir 516, in which the surface of the drug-releasing layer is covered by a rate-controlled polymeric membrane. A "drug reservoir," as used in the disclosure, is the homogenous dispersion of drug within a matrix. A drug reservoir may include a concentration of one or more ingredients including but not limited to an ovarian support cell, a prescription drug product, a supplement, a chemical ingredient and the like. For example, a drug may include a plurality of encapsulated engineered ovarian cells 516. Drug reservoir 516 may be a solid, solid dispersion, or a drug solution in liquid form. Pore 508 size of the membrane may allow for transmission of hormones secreted from encapsulated engineered ovarian support cell 512 out of the ECM and into the hormonal environment of the user in a bi-directional flow as described above in more detail. In an embodiment, pore 508 may not allow for an engineered ovarian support cell 512 to pass, thereby preventing bi-directional flow of the engineered ovarian support cell. The encapsulation process for preparing the drug formulation inside the reservoir compartment includes fabrication by microencapsulation, coating, and molding techniques. Microencapsulation is a process in which tiny particles or droplets are surrounded by a coating to give small capsules, with useful properties. In general, it is used to incorporate food ingredients, enzymes, cells or other materials on a micro metric scale. Microencapsulation can also be used to enclose solids, liquids, or gases inside a micrometric wall made of hard or soft soluble film, to reduce dosing frequency and prevent the degradation of pharmaceuticals. In its simplest form, a microcapsule is a small sphere comprising a near-uniform wall enclosing some material. The enclosed material in the microcapsule is referred to as the core, internal phase, or fill, whereas the wall is sometimes called a shell, coating, or membrane. Some materials such as but not limited to lipids and polymers, such as alginate, may be used as a mixture to trap the material of interest inside. Most microcapsules have pores with diameters between a few nanometers and a few micrometers. Materials generally used for coating are Ethyl, cellulose, Polyvinyl, alcohol, Gelatin, Sodium alginate. Microencapsulation can be used to slow the release of a drug into the body. This may permit one controlled release dose to substitute for several doses of non-encapsulated drug and may decrease toxic side effects for some drugs by preventing high initial concentrations in the blood. There is usually a certain desired release pattern. In some cases, it is zero-order, i.e., the release rate is constant. In this case, the microcapsules deliver a fixed amount of drug per minute or hour during the period of their effectiveness. This can occur as long as a solid reservoir or dissolving drug is maintained in the microcapsule. Additionally, a thin layer of silicone or poly acrylate adhesive may be applied to the external surface of the rate controlling membrane to achieve intimate contact of the ECM and the skin surface. The polymeric membrane may be manufactured from a nonporous, microporous semipermeable membrane.

Figure 6:
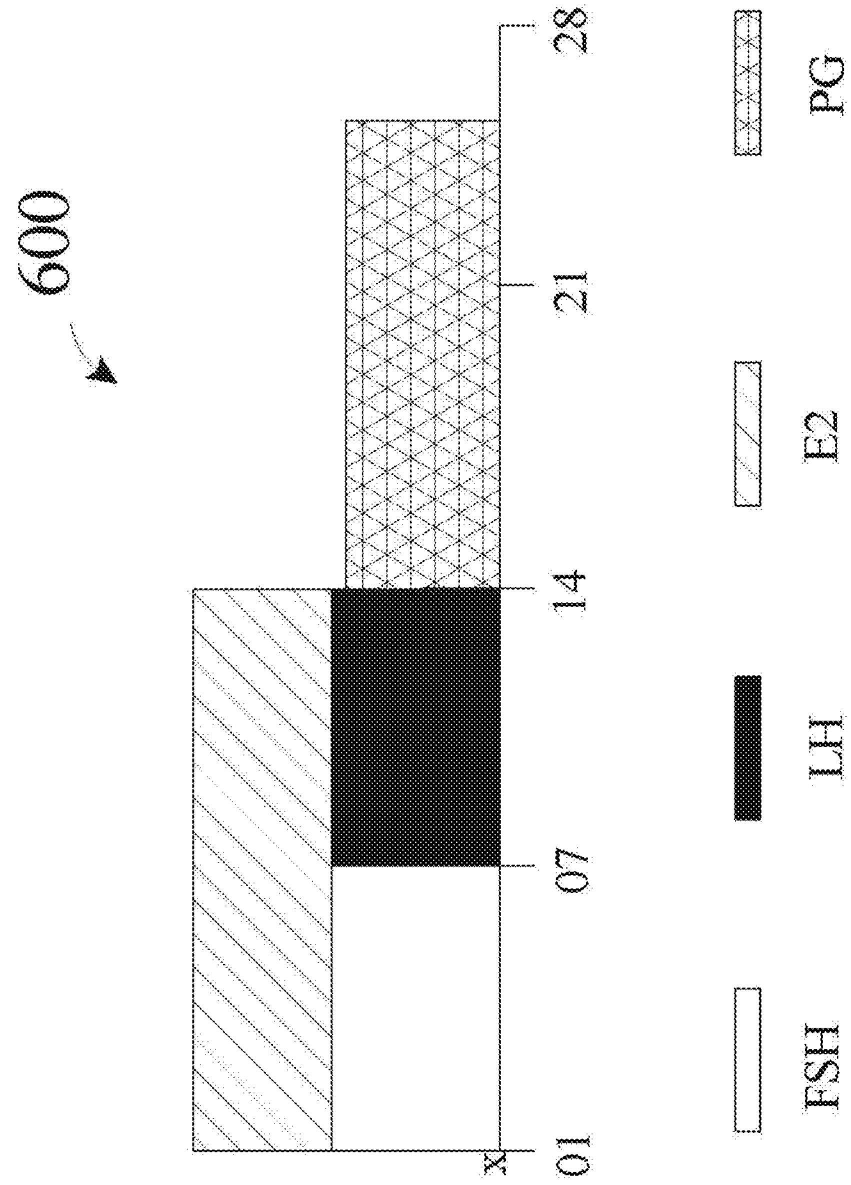
FIG. 6 is an exemplary diagram of a cyclic dosing schedule.

Referring now to FIG. 6, is an exemplary diagram of a cyclic dosing schedule, wherein the x axis line displays the number and range of days during a menstrual cycle. The x axis marks a 4 week period ranging from first week, 01-07 days, second week, 07-014 days, third week 14-21 days, up to a fourth week, 21-28 days. The implant 100, as disclosed at least in FIG. 1, may work in tandem with the ovaries to produce sufficient hormone levels. For example, a user in ovarian decline may still produce estrogen but not at sufficient levels, the implant 100 may secrete a dose of estrogen that matches the difference. In some embodiments, the implant may be the sole source of the hormone, in lieu of the ovary. On average, levels of estradiol in premenopausal women are highly variable throughout the menstrual cycle and reference ranges widely vary from source to source. Estradiol levels are minimal and according to most laboratories range from 20 to 80 pg/mL during the early to mid-follicular phase (or the first week of the menstrual cycle, also known as menses). Levels of estradiol gradually increase during this time and through the mid to late follicular phase (or the second week of the menstrual cycle) until the pre-ovulatory phase. At the time of pre-ovulation (a period of about 24 to 48 hours), estradiol levels briefly surge and reach their highest concentrations of any other time during the menstrual cycle. Circulating levels are typically between 130 and 200 pg/mL at this time, but in some women may be as high as 300 to 400 pg/mL, and the upper limit of the reference range of some laboratories are even greater (for instance, 750 pg/mL). Following ovulation (or mid-cycle) and during the latter half of the menstrual cycle or the luteal phase, estradiol levels plateau and fluctuate between around 100 and 150 pg/mL during the early and mid-luteal phase, and at the time of the late luteal phase, or a few days before menstruation, reach a low of around 40 pg/mL.

Still referring to FIG. 6, in women, progesterone levels are relatively low during the preovulatory phase of the menstrual cycle, rise after ovulation, and are elevated during the luteal phase, as shown in the diagram above. Progesterone levels tend to be less than 2 ng/mL prior to ovulation and greater than 5 ng/mL after ovulation. If pregnancy occurs, human chorionic gonadotropin is released, maintaining the corpus luteum and allowing it to maintain levels of progesterone. Between 7 and 9 weeks, the placenta begins to produce progesterone in place of the corpus luteum in a process called the luteal-placental shift. Luteinizing hormone (LH) levels are normally low during childhood and in women, high after menopause. Since LH is secreted as pulses, it is necessary to follow its concentration over a sufficient period of time to get proper information about its blood level. During reproductive years, typical levels are between 1 and 20 IU/L. Physiologic high LH levels are seen during the LH surge and typically last 48 hours. Follicle stimulating hormone levels are typically measured in the early follicular phase of the menstrual cycle, day three to five, counted from last menstruation. At this time, the levels of estradiol (E2) and progesterone are at the lowest point of the menstrual cycle. FSH levels in this time is often called basal FSH levels, to distinguish from the increased levels when approaching ovulation. The mean values for women before ovulation are around (3.8-8.8) mUI/mL. After ovulation these levels drop to between (1.8-5.1) mUI/mL. At the mid of the menstrual cycle, it reaches its highest value, between (4.5-22.5) mIU/mL. During menopause, the values go up even more, between (16.74-113.59)

Still referring to FIG. 6, regarding the cyclic dosing schedule, during the first week of user's menstrual cycle, and/or the follicular phase, FSH may primarily be secreted by the engineered ovarian cell through the implant and into a user's blood stream. The follicular phase starts on the first day of menstruation and ends with ovulation. Prompted by the hypothalamus, the pituitary gland releases follicle stimulating hormone (FSH). This hormone stimulates the ovary to produce around five to 20 follicles (tiny nodules or cysts), which bead on the surface. A user experiencing ovarian decline may not be able to produce a sufficient amount of FSH, in response to this, the implant may release the FSH in the pituitary glands please. For example, the implant may secrete 1.4 to 9.9 IU/mL of FSH hormones. During this phase, 551-2753 pmol/L of E2 may also be secreted from the implant. During the second week and/or ovulation phase of the menstrual cycle, LH may primarily be secreted by the engineered ovarian cell through the implant and into a user's blood stream. Ovulation is the release of a mature egg from the surface of the ovary. This usually occurs mid-cycle, around two weeks or so before menstruation starts. During the follicular phase, the developing follicle causes a rise in the level of estrogen. The hypothalamus in the brain recognizes these rising levels and releases a chemical called gonadotrophin-releasing hormone (GnRH). This hormone prompts the pituitary gland to produce raised levels of luteinizing hormone (LH) and FSH. In response to this brain signaling, the implant may secrete 21.9-56.6 IU/L of LH. During ovulation, the egg bursts from its follicle, but the ruptured follicle stays on the surface of the ovary. For the next two weeks or so, the follicle transforms into a structure known as the corpus luteum. This structure starts releasing progesterone, along with small amounts of estrogen. This combination of hormones maintains the thickened lining of the uterus, waiting for a fertilized egg to stick (implant). In this phase of ovulation, implant 100 may primarily secrete 2 to 25 ng/mL of progesterone. Secretion of a hormone may stop based on chemical singling of the hypothalamus through the blood stream.

Figure 7:
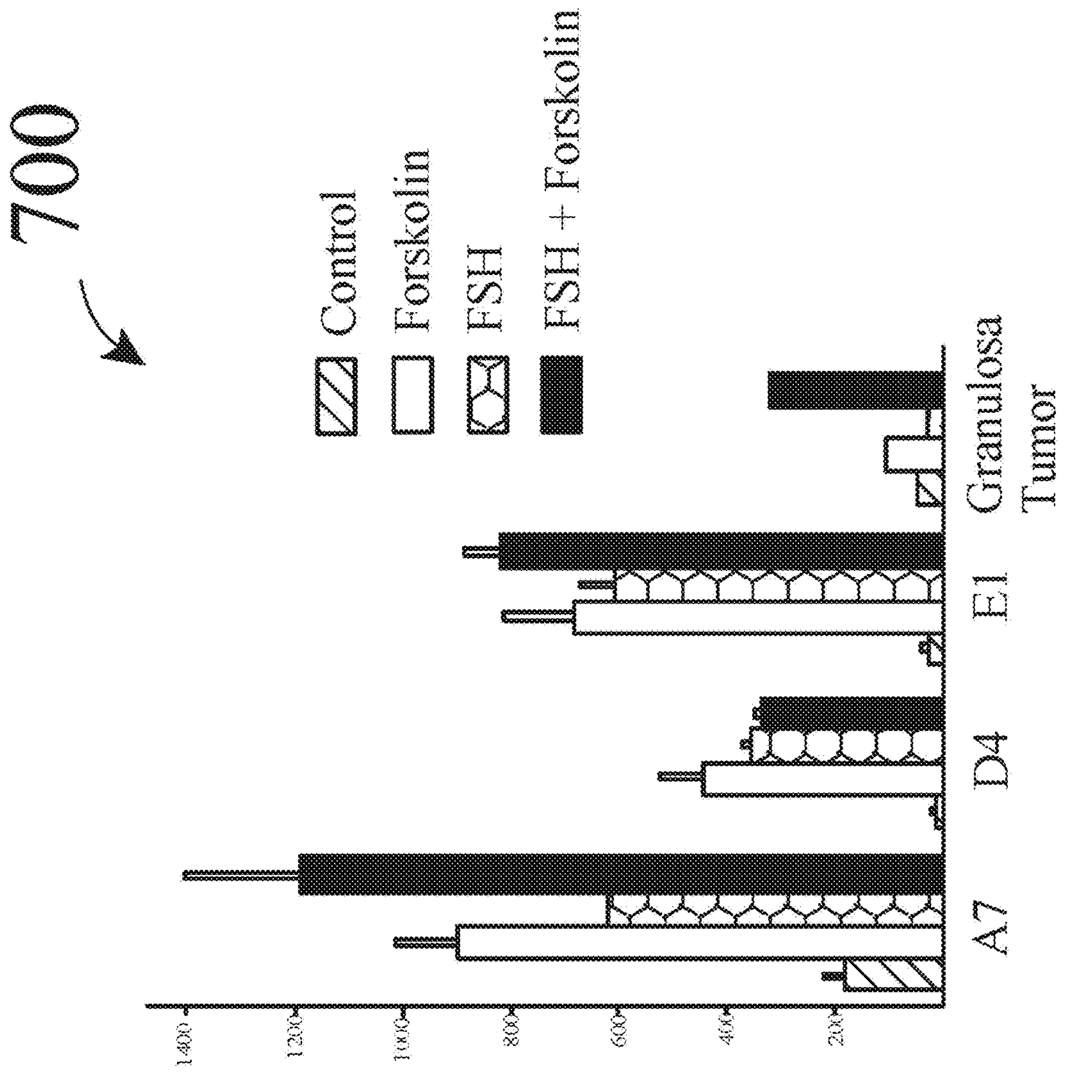
FIG. 7 an exemplary graph illustrating production rates of estradiol from engineered ovarian support cells.

Referring now to FIG. 7, an exemplary graph 700 illustrating production rates of estradiol (E2) from engineered ovarian support cells configured to produce one or more hormones prevalent in ovarian health is illustrated. E2 levels were measured in pg/uL. Graph shows the E2 production rate from engineered ovarian support cells: A7, D4, E1 compared to a granulosa tumor in response to stimuli. Stimuli includes control, forskolin, FSH, and FSH+Forskolin. The granulosa tumor is a tumor that arise from granulosa cells. It is estrogen secreting and present as large, complex, ovarian mass. The granulosa tumor is part of the sex cord-gonadal stromal tumor or non-epithelial group of tumors. Regarding the forskolin stimulus, forskolin (coleonol) is a labdane diterpene produced by the plant *Coleus barbatus* (Blue Spur Flower). Forskolin contains some unique functional elements, including the presence of a tetrahydropyran-derived heterocyclic ring. Forskolin is commonly used in biochemistry to raise levels of cyclic AMP (cAMP) in the study and research of cell physiology. Forskolin activates the enzyme adenylyl cyclase and increases intracellular levels of cAMP. cAMP is an important second messenger necessary for the proper biological response of cells to hormones and other extracellular signals. It is required for cell communication in the hypothalamus/pituitary gland axis and for the feedback control of hormones via induction of corticotropin-releasing factor gene transcription. Cyclic AMP acts by activating cAMP-sensitive pathways such as protein kinase A and EPAC1. Its derivatives include colforsin daropate, NKH477, and FSK88, which may be more potent than forskolin at raising cAMP. These derivatives may have pharmaceutical utility against bronchoconstriction and heart failure. Regarding the FSH stimulus, Follicle-stimulating hormone (FSH) is a gonadotropin, a glycoprotein polypeptide hormone. FSH is synthesized and secreted by the gonadotropic cells of the anterior pituitary gland and regulates the development, growth, pubertal maturation, and reproductive processes of the body. FSH stimulates the growth and recruitment of immature ovarian follicles in the ovary. FSH initiates follicular growth, specifically affecting granulosa cells.

Still referring to FIG. 7, the engineered cells exposed to the control produced up to 200 pg/uL of E2. When exposed to Forskolin, around 900 pg/uL of E2. In response to FSH, up to pg/uL of E2. In response to FSH+Forskolin, up to 1200 pg/uL of E2. A7 showed the most significant E2 production rates, while the granulosa tumor, at the most, produced around 300 pg/uL of E2 when exposed to FSH+Forskolin.

What is claimed is:

1. A method of administering an implant for ovarian decline to a human subject diagnosed as having ovarian decline, the method comprising:
- locating an administration site; and
- inserting the implant at the administration site, wherein the implant comprises:
  - at least an engineered ovarian support cell;
  - an extracellular matrix substrate; and
  - a delivery apparatus.

2. A method of administering an implant for ovarian decline to a human subject diagnosed as having ovarian decline in claim 1, the method comprising:
- locating an administration site; and
- inserting the implant at the administration site, wherein the administration site is between the epidermis and dermis skin layers.

3. A method of administering an implant for ovarian decline to a human subject diagnosed as having ovarian decline in claim 1, the method comprising:
- locating an administration site; and
- inserting the implant at the administration site, wherein the administration site is at a layer of skin.

* * * * *